United States Patent
Chang et al.

(10) Patent No.: US 9,044,582 B2
(45) Date of Patent: Jun. 2, 2015

(54) APPARATUS AND METHOD FOR TRANSDERMAL FLUID DELIVERY

(71) Applicants: Franklin J. Chang, Pasadena, CA (US); Henry Ping Chang, San Marino, CA (US)

(72) Inventors: Franklin J. Chang, Pasadena, CA (US); Henry Ping Chang, San Marino, CA (US)

(*) Notice: Subject to any disclaimer, the term of this patent is extended or adjusted under 35 U.S.C. 154(b) by 0 days.

(21) Appl. No.: 14/257,288

(22) Filed: Apr. 21, 2014

(65) Prior Publication Data

US 2015/0088050 A1 Mar. 26, 2015

Related U.S. Application Data

(63) Continuation-in-part of application No. 13/533,719, filed on Jun. 26, 2012, now abandoned.

(51) Int. Cl.
*A61M 37/00* (2006.01)
*A61N 1/32* (2006.01)
*A61B 18/00* (2006.01)

(52) U.S. Cl.
CPC ........... *A61M 37/00* (2013.01); *A61M 37/0015* (2013.01); *A61M 2037/0007* (2013.01); *A61M 2037/0061* (2013.01); *A61N 1/328* (2013.01); *A61N 1/325* (2013.01); *A61B 2218/001* (2013.01); *A61B 2018/00452* (2013.01); *A61N 1/327* (2013.01); *A61B 2217/005* (2013.01)

(58) Field of Classification Search
CPC ............. A61B 17/3207; A61B 17/545; A61B 2017/00765; A61B 2018/00452; A61B 2217/005; A61B 2218/001; A61M 37/00; A61M 2037/0007; A61N 1/328; A61N 1/325; A61N 1/327

USPC ........ 604/501, 34, 500, 20, 22; 606/131, 132, 606/32–41, 43

See application file for complete search history.

(56) References Cited

U.S. PATENT DOCUMENTS

| | | | | |
|---|---|---|---|---|
| 6,689,103 | B1* | 2/2004 | Palasis | 604/173 |
| 6,743,215 | B2* | 6/2004 | Bernabei | 604/500 |
| 7,422,567 | B2* | 9/2008 | Lastovich et al. | 604/46 |
| 7,658,742 | B2* | 2/2010 | Karasiuk | 606/131 |
| 8,386,027 | B2* | 2/2013 | Chuang et al. | 600/547 |
| 2001/0009984 | A1* | 7/2001 | Nemati | 604/22 |
| 2001/0023351 | A1* | 9/2001 | Eilers et al. | 606/131 |
| 2002/0099356 | A1* | 7/2002 | Unger et al. | 604/501 |
| 2003/0093040 | A1* | 5/2003 | Mikszta et al. | 604/289 |
| 2004/0064087 | A1* | 4/2004 | Lastovich et al. | 604/46 |
| 2006/0264893 | A1* | 11/2006 | Sage | 604/501 |
| 2008/0139995 | A1* | 6/2008 | Guerra | 604/22 |
| 2008/0275378 | A1* | 11/2008 | Herndon | 604/22 |
| 2008/0275468 | A1* | 11/2008 | Chuang et al. | 606/131 |
| 2009/0043293 | A1* | 2/2009 | Pankratov et al. | 606/9 |
| 2009/0048557 | A1* | 2/2009 | Yeshurun et al. | 604/20 |

(Continued)

*Primary Examiner* — Theodore Stigell
*Assistant Examiner* — Amber Stiles

(57) ABSTRACT

An apparatus for transdermal fluid delivery includes a handle and a tip, having a skin applying surface, being driven to move by a driving unit. A fluid delivery structure has an aperture formed at the skin applying surface and a vacuum entry port. An abrading structure, an electrode structure, and a microneedling structure are selectively provided at the skin applying surface with the fluid delivery structure to provide multiple functions of the tip. A flow of fluid is delivered onto the skin applying surface through the fluid delivery structure to interact with the abrading elements and the electrodes before the fluid is returned and collected, so that three different skin treatments of abrasive peeling, electrical stimulation, and liquid infusion are achieved in one single structure for improving a skin structure.

10 Claims, 19 Drawing Sheets

(56) References Cited

U.S. PATENT DOCUMENTS

| | | | |
|---|---|---|---|
| 2009/0149797 A1* | 6/2009 | Dacey, Jr. et al. | 604/20 |
| 2010/0049177 A1* | 2/2010 | Boone et al. | 606/9 |
| 2010/0130972 A1* | 5/2010 | Yambor et al. | 606/34 |
| 2011/0009882 A1* | 1/2011 | Remsburg et al. | 606/131 |
| 2013/0137951 A1* | 5/2013 | Chuang et al. | 600/364 |

* cited by examiner

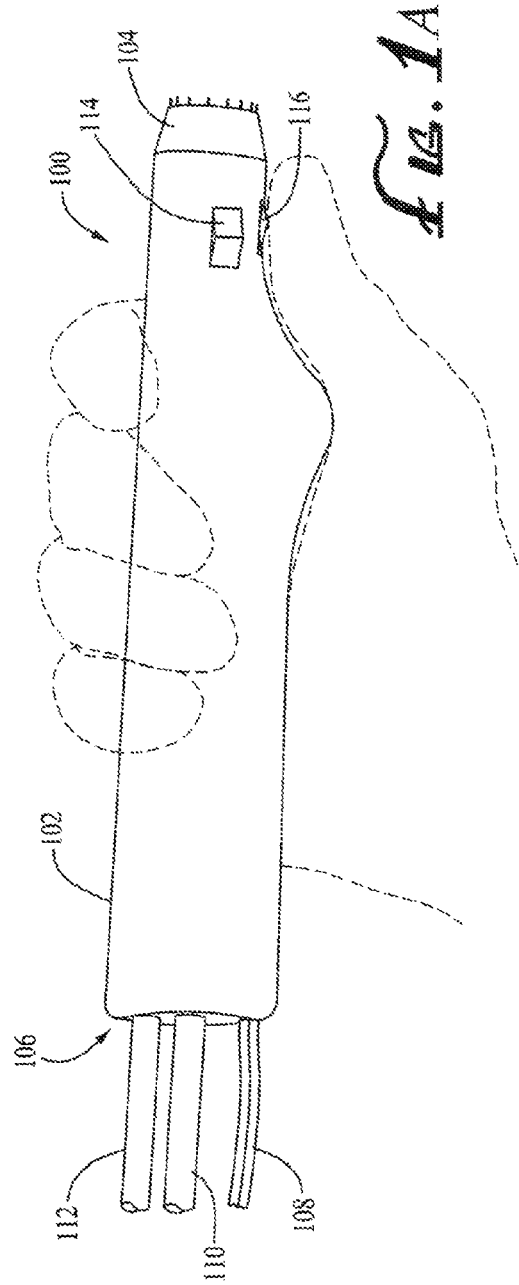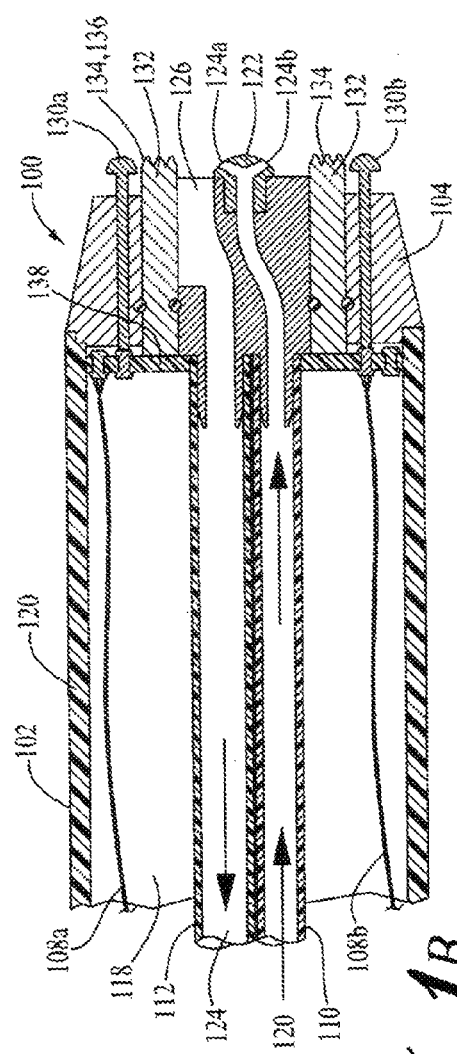

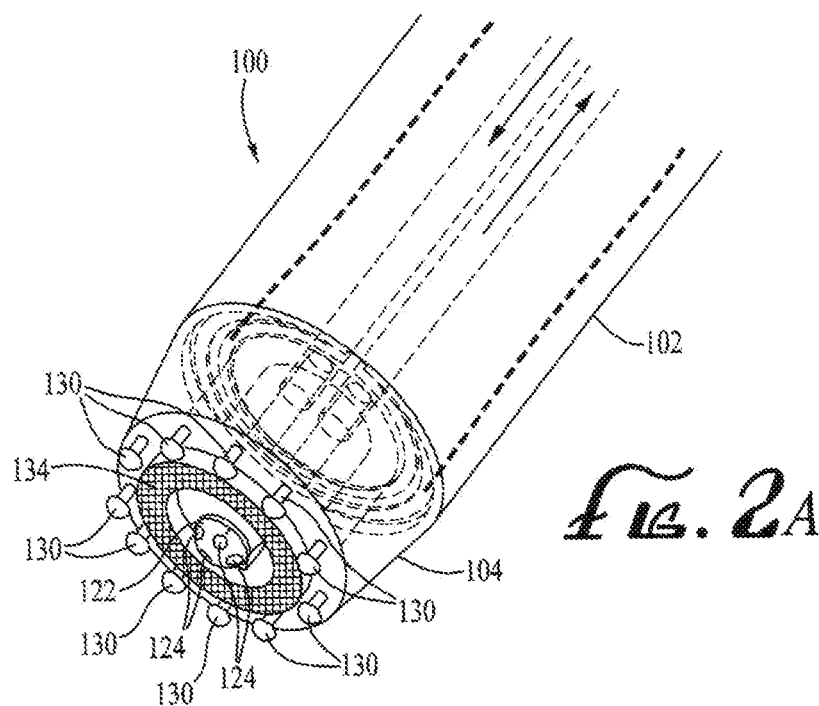
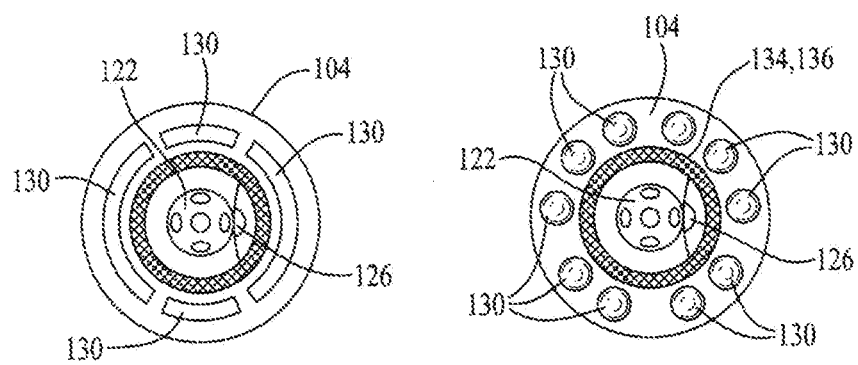

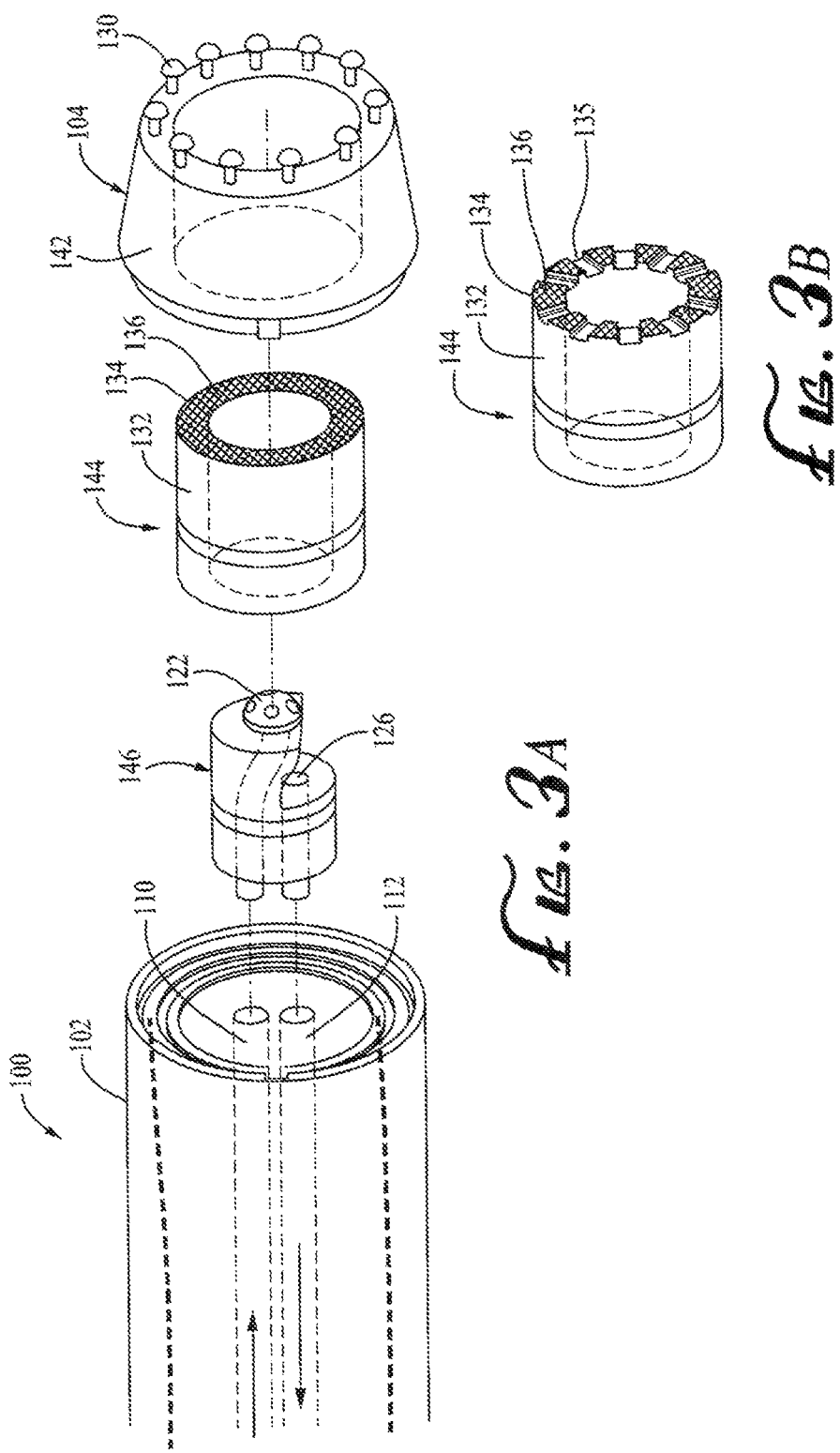

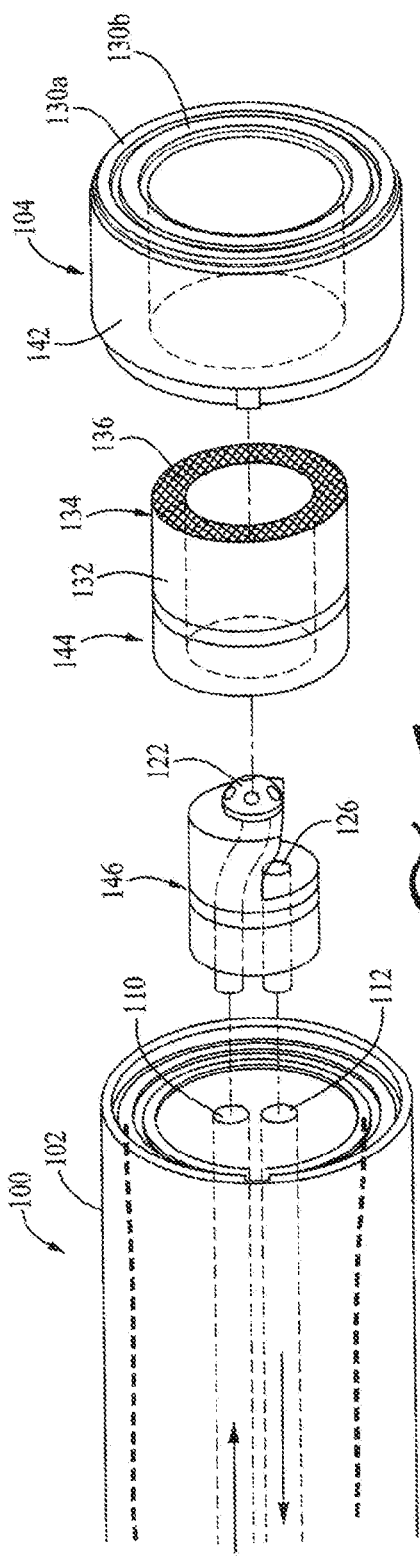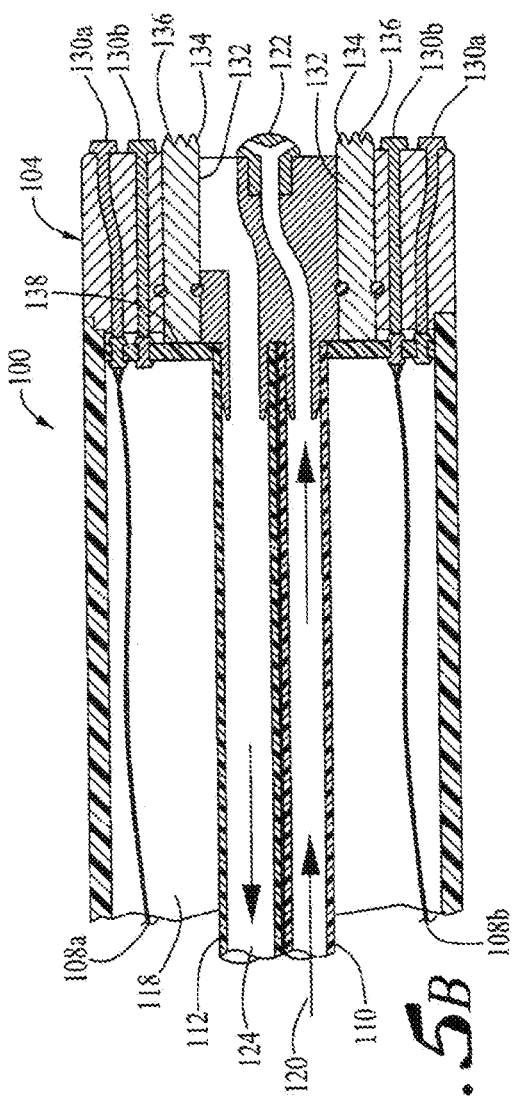

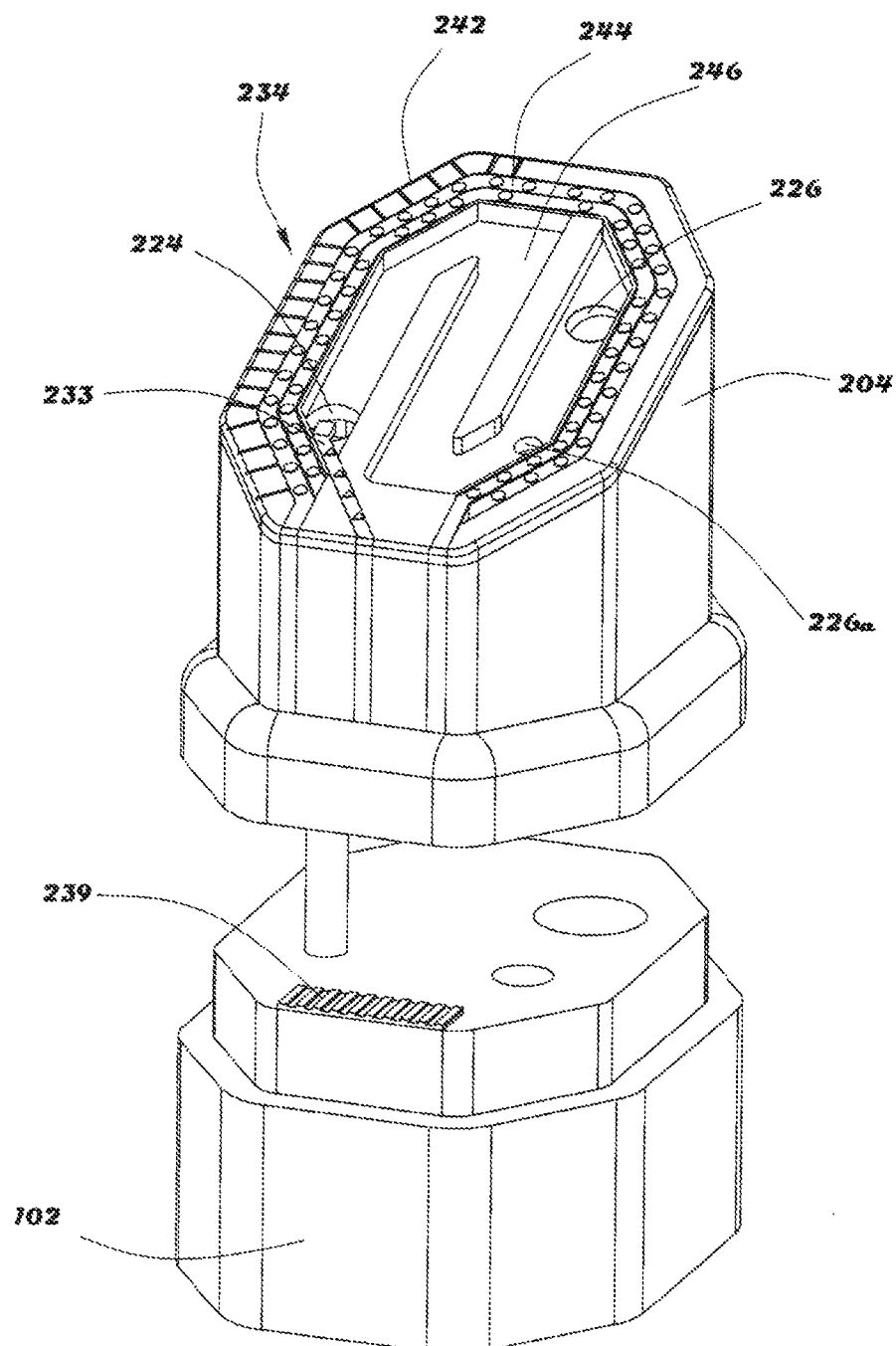

APPARATUS AND METHOD FOR TRANSDERMAL FLUID DELIVERY

CROSS REFERENCE WITH RELATED APPLICATION

This is a CIP application of a non-provisional application Ser. No. 13/683,995 and filed Nov. 21, 2012, which is a continuation application of a non-provisional application Ser. No. 13/533,719 and filed Jun. 26, 2012.

BACKGROUND

1. Field of the Invention

The present invention relates to a skin treatment tool. More particularly, the present invention relates to an apparatus and method for transdermal fluid delivery.

2. Discussion of the Related Art

Current techniques for superficial skin resurfacing, known as microdermabrasion, treat the outer epidermal layer of the skin by removing the superficial layer to induce the body's own natural wound healing response. It is known in the art to couple microdermabrasion with fluid delivery to enhance therapeutic effects. However, combined microdermabrasion/fluid delivery treatments are hindered by the protective barrier function of the stratum corneum which limits the depth of penetration and absorption to the surface of the skin when drugs and/or fluids are applied to the skin.

Other techniques for skin enhancing include transdermal drug delivery employing an electrical current (e.g., skin electroporation) are known. However, these techniques have limited results based on: 1) the lack of an efficient fluid supply/return system using a vacuum; 2) the impedance of the stratum corneum which limits the efficacy of the current technologies of electrical penetration of drugs and/or fluids; and 3) the optimal permeation structure of the skin occurs during application of an electrical current and only lasts a few seconds after application of the electrical pulse.

Known technologies for delivery of an electro-current, to the skin suffer from one or more of the following deficiencies which lead to limited results, including, a lack of an efficient fluid supply/return system using a vacuum source; an inability to simultaneously apply fluid and electro-current to the skin; as a means to lower the impedance of the stratum corneum.

The major disadvantage of the conventional art is that the fluid cannot be directly applied from on the abrading surface to the skin. An injection end of a tube is extended close but separate to the abrading surface so that the fluid is injected to the abrading surface through the injection end. The fluid flowing through injection end will not be evenly distributed the fluid on the abrading surface when applying on the skin. Most of the fluid in fact will never be in contact with the skin and be wasted because the fluid cannot fully penetrate between the skin and the abrading surface of the skin. More importantly, the individual injection tube structure is used when there is a motor utilized in the microdermabrasion device.

US. Pub. No. 2010/0049177 A1 Boone, discloses a microdermabrasion system which comprises a tip having an abrading surface and a side surface, wherein a plurality of fluid channels terminate on the side surface of the tip. That is to say, the fluid cannot be directly delivered through the abrading surface of the tip. Boone further discloses a plurality of radiation sources evenly distributed around a perimeter of the tip and between the tip and the vacuum opening. This structure has a major disadvantage that the fluid will only deliver to the radiation sources but not the abrading surface because of the vacuum effect at the vacuum opening. Therefore, the user must hold the hand piece of Bonne to manually move to the tip on the skin. Also, Boone describes using radio frequency to heat below the skin but does not describe any relationship to the fluid delivery or abrasive. It is a means to penetrate heat into deeper layers to cause tightening of the skin but do not create a transdermal pathway for fluid. This type of frequency also has no relationship with abrasion and liquid.

US. Pub. No. 2004/0138680 A1 Twitchell et al., disclosed a microdermabrasion apparatus comprising an exfoliation tip mechanically coupled to a motor via a shaft and a tube extended to a vacuum pace in the suction cup. The suction cup as taught by Twitchell et al. is arranged in such a way that the user's skin is pulled partially into the suction cup where a vacuum is formed within the space in the suction cup. That is to say, no fluid is applied onto the exfoliation tip and no fluid is sucked back via the tube.

U.S. Pat. No. 8,343,116, Ignon et al., disclosed a skin treatment system comprising a tip having at least one abrasive element configured to abrade skin, a delivery port and a suction port extended to a working surface of the tip, wherein the delivery port delivers fluid from a first canister to the working surface of the tip and the suction port sucks the fluid back to a second canister from the working surface of the tip. The disadvantage of the system as taught by Ignon et al. is that the fluid will be sucked back by the suction port right after the fluid is delivered to the working surface of the tip. That is to say, the fluid will not be applied long enough on the working surface of the tip. Also, without any motor incorporated within the system as taught by Ignon et al., the user must hold the hand piece of Ignon et al. to manually move the tip over the skin in a scratching motion. Thus, the system as taught by Ignon et al. makes it impossible to incorporate with any electrodes because both the delivery port and suction port are located right at the working surface of the tip. So the fluid cannot be delivered to be in contact with any electrode after it is vacuumed back by the suction port.

Accordingly, there is a need for a skin resurfacing and enhancement system with an enhanced fluid delivery/fluid return capacity which also improves the permeation structure of the skin. The present invention discloses an apparatus and method for transdermal fluid delivery which provides three different skin treating functions for skin treatment to transdermally penetrate fluid deeper into the skin by means of simultaneous 1) abrasive peeling 2) electrical stimulation 3) liquid infusion in order to improve the skin structure affecting multiple layers of the skin, such as the epidermis, dermis, and hypodermis. The present invention also provides an innovative structure to simultaneously guide the fluid to the tip surface and to prolong the traveling path of the fluid.

BRIEF SUMMARY OF THE INVENTION

According to the present invention, devices and methods for a combination treatment of the top and bottom layer of a skin surface are described. The device comprises transdermal drug and/or fluid delivery with electrodes providing electric current to stimulate the skin, and an abrasive tip to peel the top layer of skin simultaneously applied to the skins surface. According to one embodiment of the present invention, a skin treatment device that combines a fluid delivery system, an abrasive tip, and an electric current delivery probe in one handle is described. Preferably the device further comprises a vacuum source for removal of fluid and skin debris from the surface of the skin.

According to the present invention, it discloses the method and apparatus of treating the skin to transdermally penetrate fluid deeper into the skin by means of simultaneous 1) abrasive peeling 2) electrical stimulation 3) liquid infusion to improve the skin structure affecting multiple layers of the skin, such as, epidermis, dermis, and hypodermis. The apparatus of the present invention serves as an all-in-one handheld skin treatment device.

The device and methods described herein allow for the simultaneous deep penetration of fluid through the skin by applying an electric current and an abrasive media in the working end of the device to increase skin's permeability. According to alternate embodiments, techniques known as electroporation, ultrasound, and other electrical induced therapies, etc., which use electric currents to go deeper past the stratum corneum to stimulate cells underneath the skin may be employed in the device. The combination of the electrical induced therapies and microdermabrasion create aqueous pathways to increase the permeability of the drugs and/or fluids which are delivered from a supply and return reservoir by a vacuum system within the device. A pressure mechanism may also be employed as part of the device.

According to one embodiment, a device for treating a skin surface of a patient comprising a handle having a tip at the proximal end of the handle is provided. The tip has one or more electrodes and an abrading end portion which has an abrasive media and one or more apertures for fluid delivery. The device may also have a vacuum and a vacuum entry port located on the tip at the proximal end of the handle, where the vacuum entry port has one or more apertures for evacuating fluid and debris from the surface of the skin. According to another embodiment, the electrodes, abrading end portion and fluid delivery apertures are positioned on the tip of the handle, where each one individually may be on a removable tip or end structure. When the device has a plurality of removable structures, the end structures may also be separately removable and interchangeable.

In a preferred embodiment, the tip of the device has an outer structure having one or more electrodes and an intermediate structure having an abrading end portion, where the abrading end portion has an abrasive media. The tip of the device also has an inner structure which has one or, more apertures for fluid delivery. That is to say, the inner structure is located at the center of the tip. The outer structure is located at the periphery of the tip. The intermediate structure is located between the inner structure and the outer structure. The outer structure, intermediate structure, and the inner structure are coaxial with each other and are in a ring shape. Preferably, the outer structure and intermediate structure form an outer ring and intermediate ring respectively at the tip. The outer ring and intermediate ring can be formed in a circular shape or a non-circular shape. Therefore, the abrading end portion forms at the intermediate ring and encircles the fluid delivery. The electrodes are aligned at the outer ring to encircle the abrading end portion at the intermediate ring. Preferably, at least one of the structures is removable, and more preferably, each of the outer structure, intermediate structure, and inner structure are removable, and most preferably, at least one of the structures is disposable.

According to another embodiment, a method for treating a skin surface of a patient is provided. According to the method, first an abrasion device for treating a skin surface of a patient is selected, wherein the abrasion device comprises one or more electrodes, an abrading end portion having an abrasive media, and one or more apertures for fluid delivery. Next, the abrading end portion of the device is placed on the skin surface of the patient. The patient's skin is then treated by applying the abrasive media to the skin surface of the patient, delivering fluid to the skin surface of the patient, and applying an electrical current to the skin surface of the patient. The patient skin is treated with abrasive media, fluid delivery, and current delivery in the order stated above, simultaneously, or another order. Vacuum may then be applied to the skin surface of the patient.

According to another embodiment, a kit for treating a skin surface of a patient is provided. The kit comprises a skin abrading device comprising a tip, wherein the tip has at least one current delivery tip having one or more electrodes, a plurality of abrading tips, wherein each abrading tip has an end portion with an abrasive media, and wherein the plurality of abrading tips are removable from the device and interchangeable, and a fluid delivery tip having one or more apertures for fluid delivery. Preferably, the tip further comprises a vacuum entry port and also preferably, each of the plurality of abrading tips has a grit size, and the grit size varies for each abrading tip.

According to another embodiment, a device for treating a skin surface of a patient, comprises a multi-functional tip having a skin applying surface, a fluid delivery structure, and a tip driver.

The tip driver comprises a driving unit and a driving shaft operatively extended from the driving unit to the multi-functional tip, so that the driving unit is operated to generate a movement at the skin applying surface of the multi-functional tip. The driving shaft has at least a hollow portion extended to the multi-functional tip.

The fluid delivery structure is arranged to directly guide a flow of fluid on the skin applying surface of the multi-functional tip. The fluid delivery structure has a fluid channel defined at the hollow portion of the driving shaft and at least an aperture formed at the skin applying surface of said multi-functional tip to communicate with the fluid channel. Therefore, the driving shaft provides multifunction of driving the skin applying surface of the multi-functional tip to rotate and guides the fluid through the fluid channel to the skin applying surface of the multi-functional tip at the aperture at the same time.

For a more complete understanding of the present invention with its objectives and distinctive features and advantages, reference is now made to the following specification and to the accompanying drawings.

BRIEF DESCRIPTION OF THE DRAWING(S)

These and other features, aspects and advantages of the present invention will become better understood from the following description, appended claims, and accompanying figures where:

FIG. 1A shows a skin abrading device 100 according to one embodiment of the present invention;

FIG. 1B is partial side cut-away view of the device 100, shown in FIG. 1A, according to the present invention;

Figure 4:
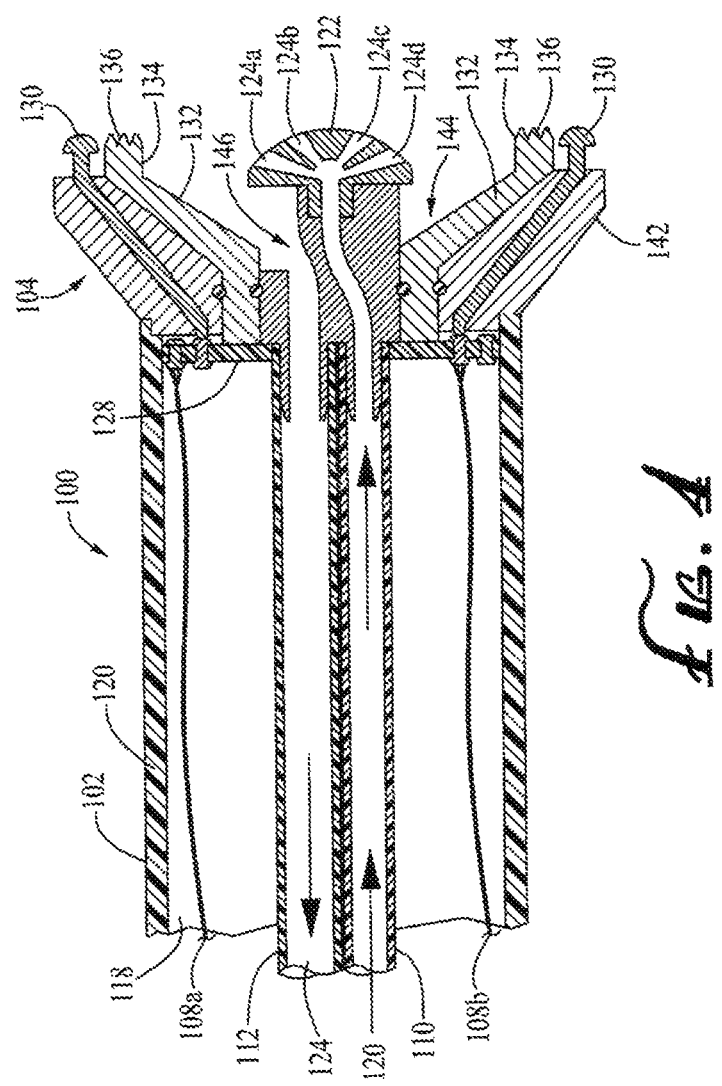
Figure 6A:
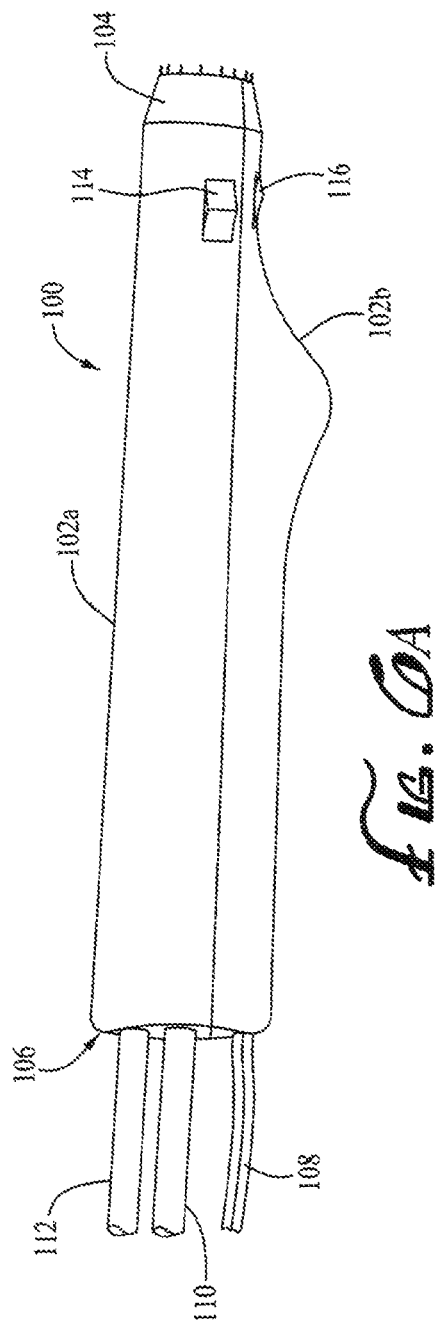
Figure 6B:
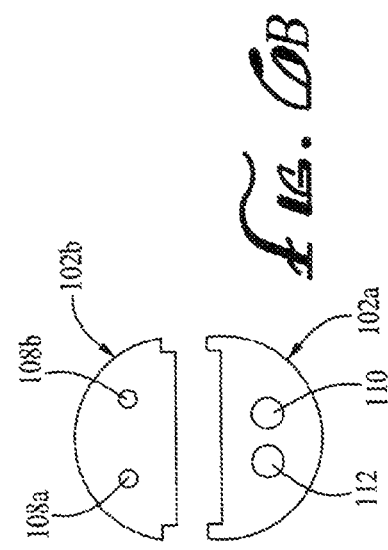

FIG. 2A is a top perspective view of the device 100, shown in FIG. 1A and FIG. 1B, showing the tip 104 of the device 100, according to the present invention;

FIG. 2B and FIG. 2C are alternate embodiments for the tip 104 of the device 100, according to another embodiment of the present invention;

FIG. 3A is a side view of one embodiment of the device 100, having a plurality of removable, exchangeable, and attachable tips according to another embodiment of the present invention;

FIG. 3B is a side view of another embodiment of one of the tips shown in FIG. 3A;

FIG. 4 is a partial side cut-away view of the device 100 having a wide-angle tip 104 according to another embodiment of the present invention;

FIG. 5A is a side view of another embodiment of the device 100, having a plurality of removable, exchangeable, and attachable tips, where the electrodes 108a, 108b, are concentric circles, according to another embodiment of the present invention;

FIG. 5B is a partial side cut-away view of the device 100 shown in FIG. 5A, having electrodes 108a, 108b, which are concentric circles, according to another embodiment of the present invention; and FIG. 6A shows an alternate embodiment of the skin abrading device 100 according to another embodiment of the present invention, having a divided handle 102a and 102b; and FIG. 6B is a cut-away view showing the divided handle 102a and 102b of FIG. 6A.

FIG. 7 is a perspective view of the tip detachably coupling at the handle according to another embodiment of the present invention.

Figure 8:
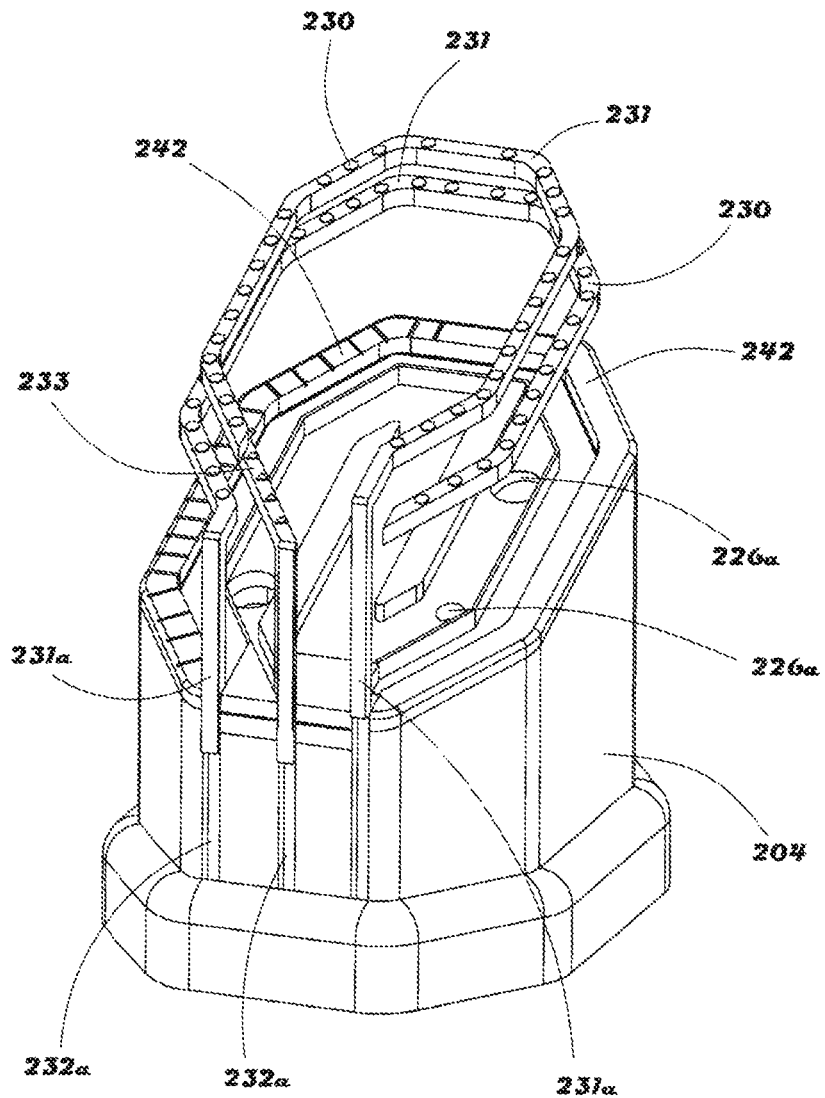

FIG. 8 is an exploded view of the tip according to the above embodiment of the present invention, showing the replacement of the electrode rings.

Figure 9:
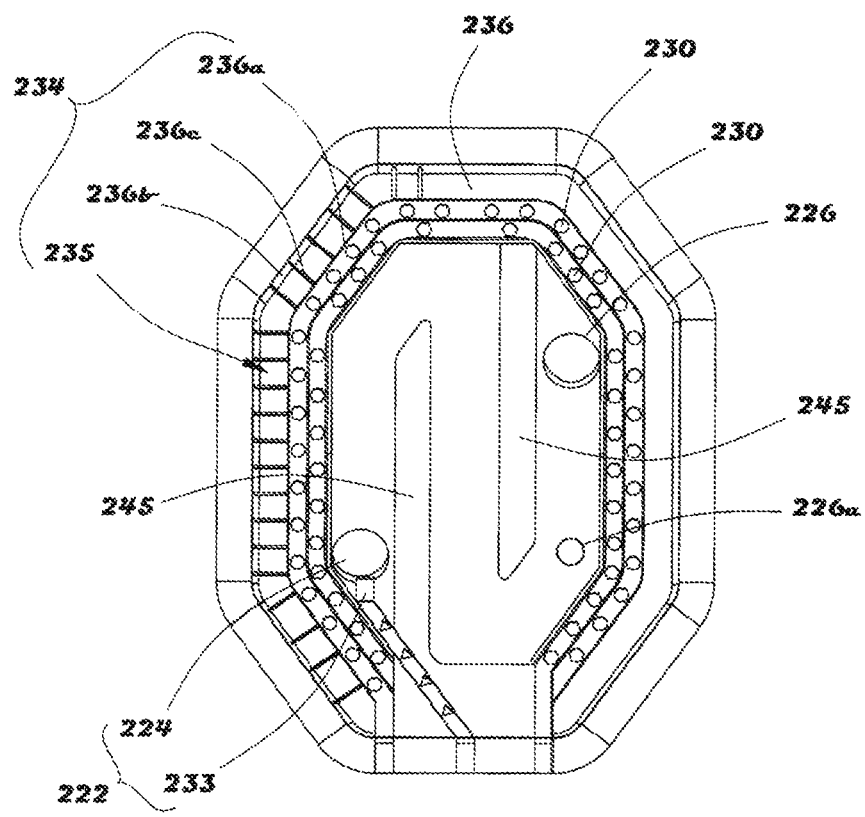

FIG. 9 is a top view of the tip according to the above embodiment of the present invention.

Figure 10:
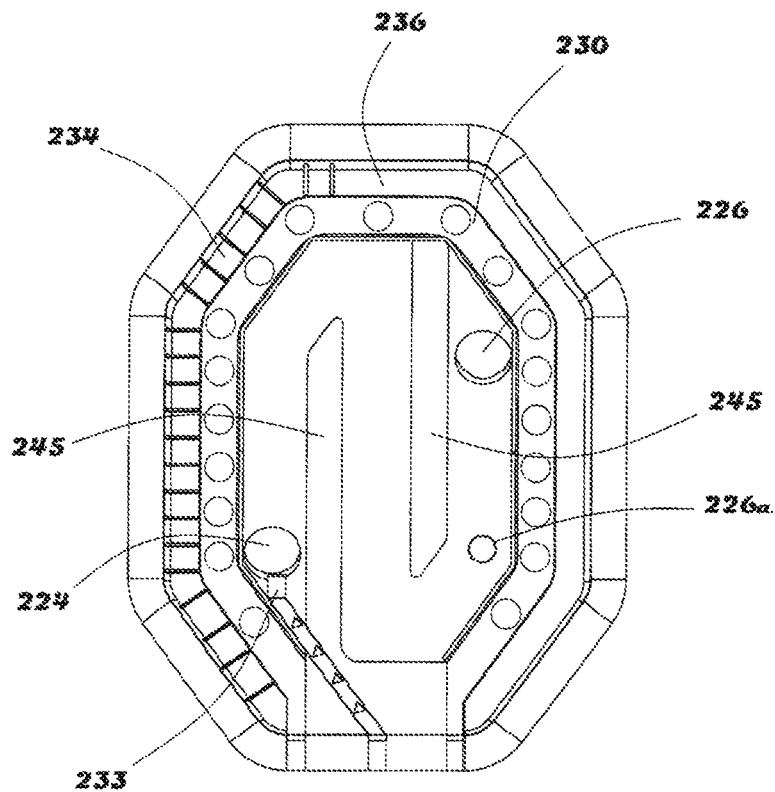

FIG. 10 is a top view of the tip according to the above embodiment of the present invention, showing one electrode ring at the intermediate structure.

Figure 11:
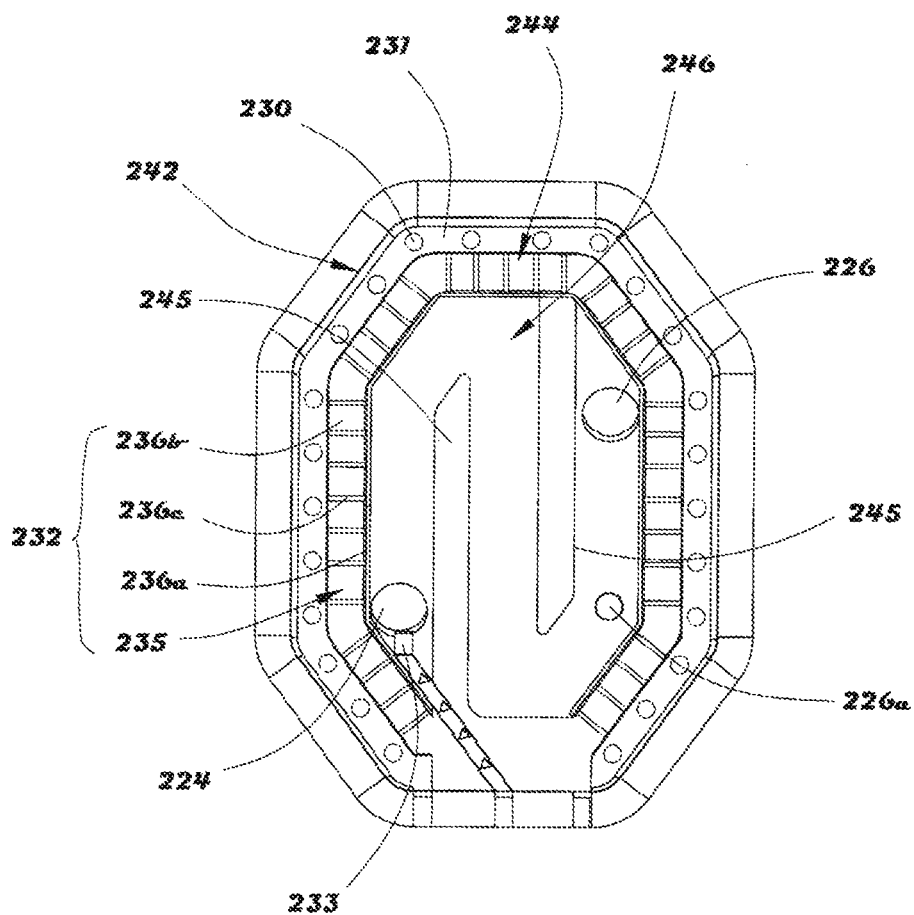

FIG. 11 is a top view of the tip according to the above embodiment of the present invention, showing the alternative of the outer and intermediate structures.

Figure 12:
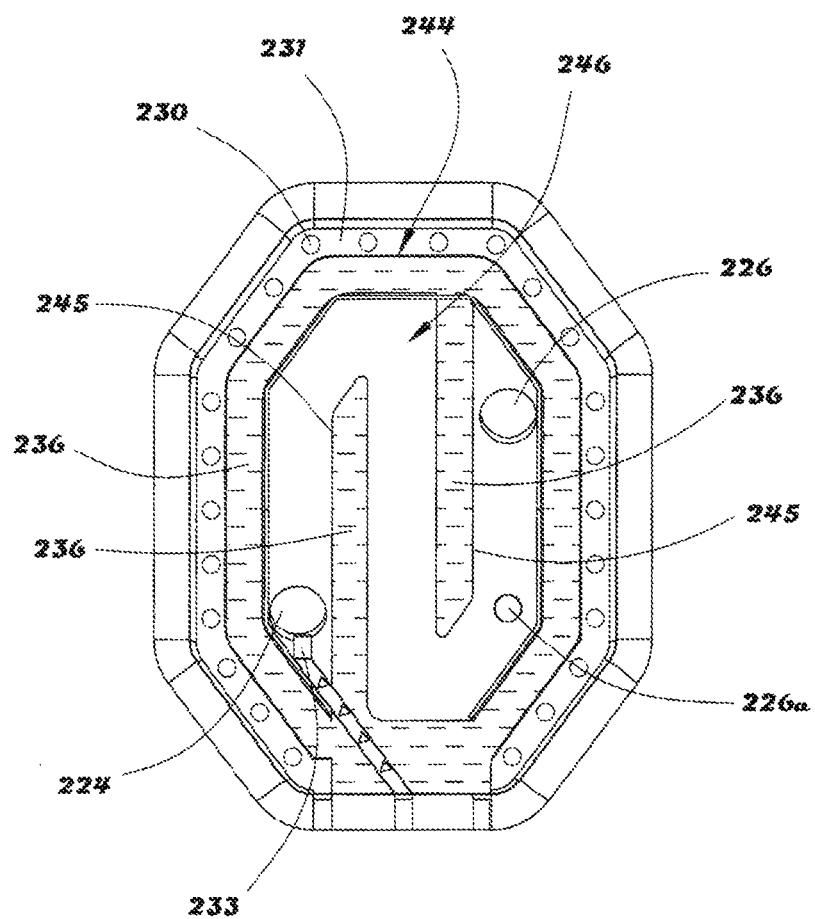

FIG. 12 is a top view of the tip according to the above embodiment of the present invention, showing how to increase the abrading surface of the tip.

Figure 13:
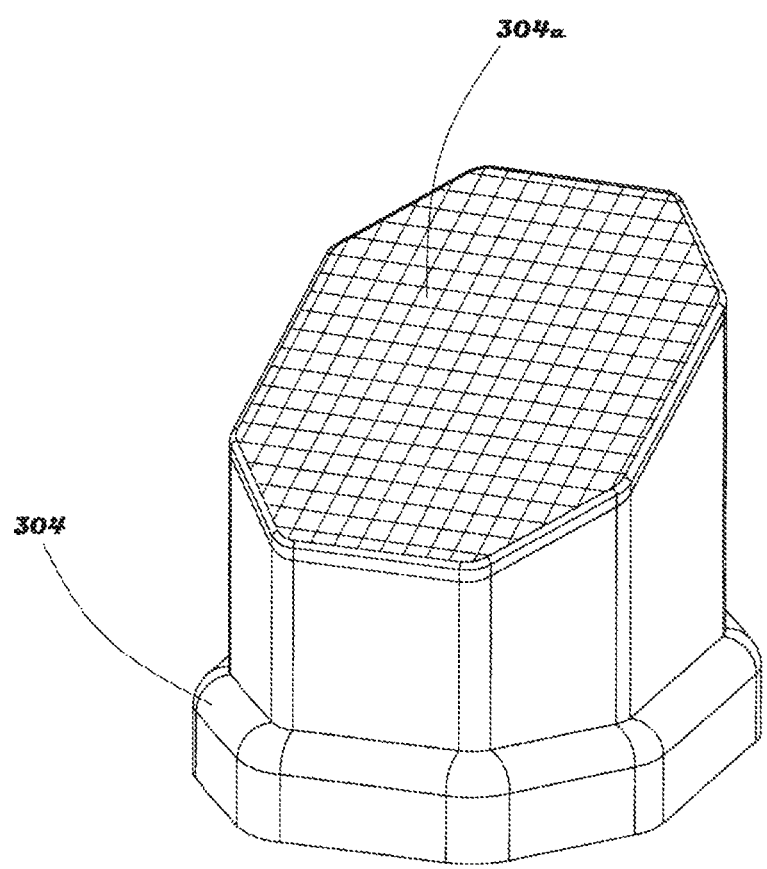

FIG. 13 is a perspective view of the tip detachably coupling at the handle according to another embodiment of the present invention, showing the electrode skin treating tip.

Figure 14:
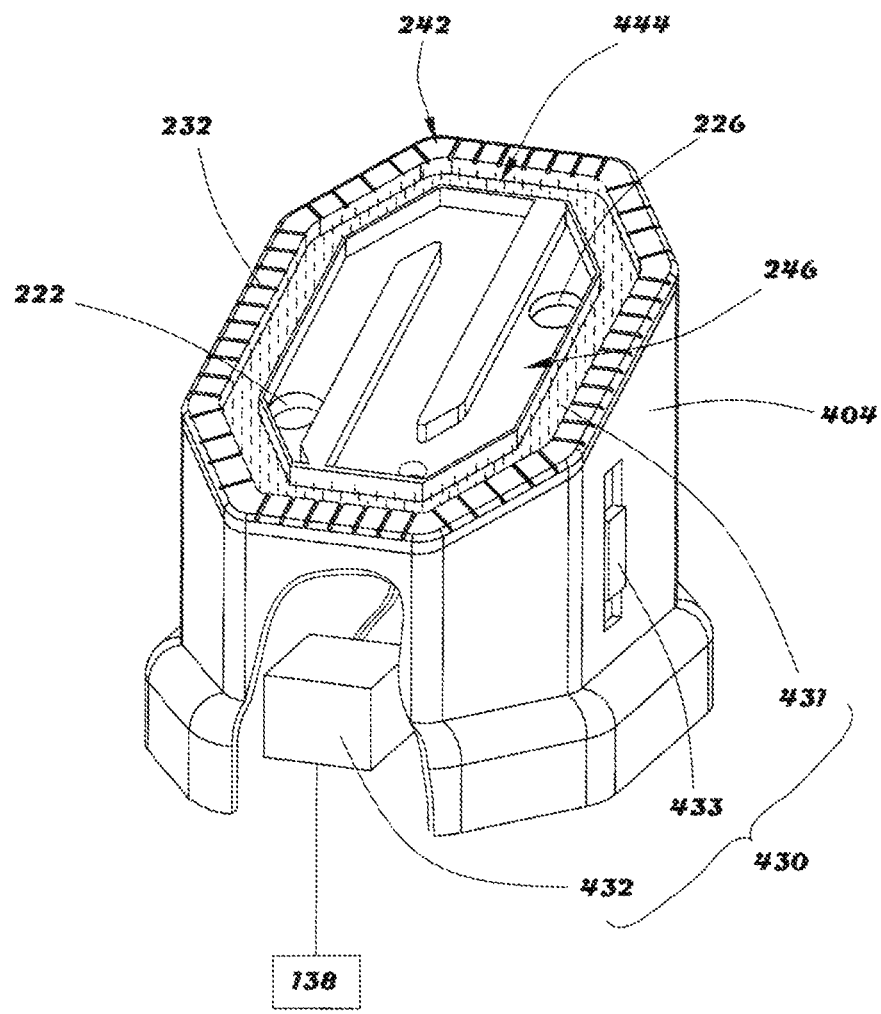

FIG. 14 is a perspective view of the tip detachably coupling at the handle according to another embodiment of the present invention, showing the micro-needle skin treating tip.

Figure 15:
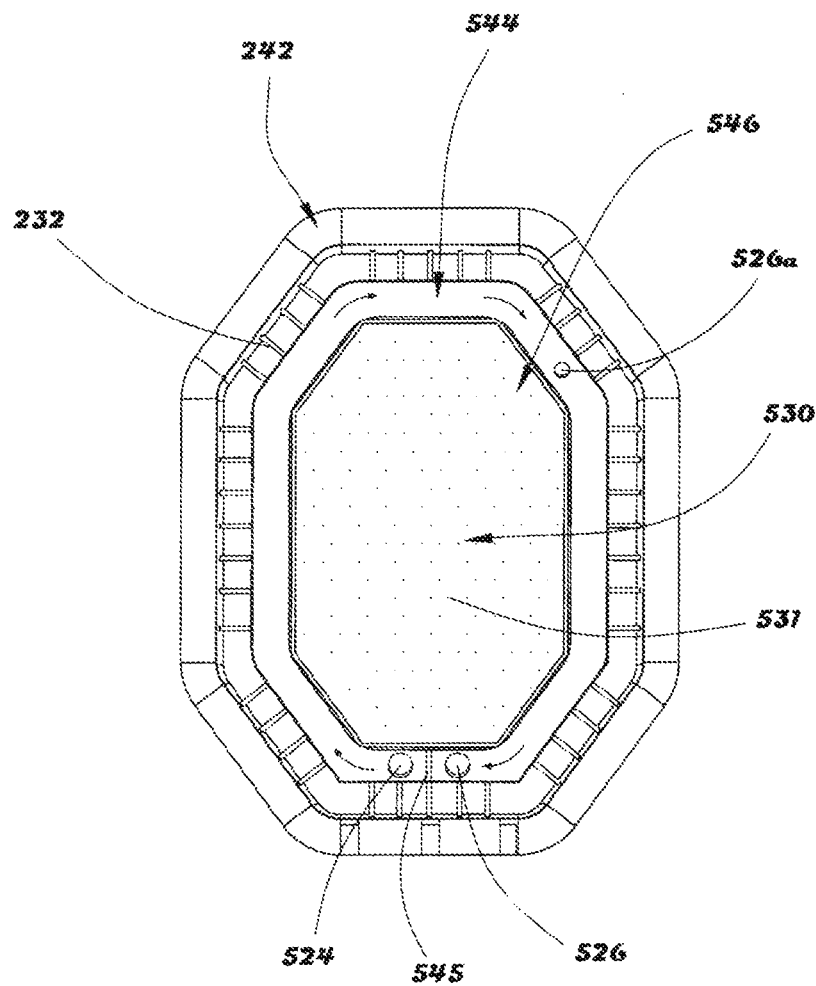

FIG. 15 is a modification of the micro-needle skin treating tip according to the above embodiment of the present invention.

Figure 16:
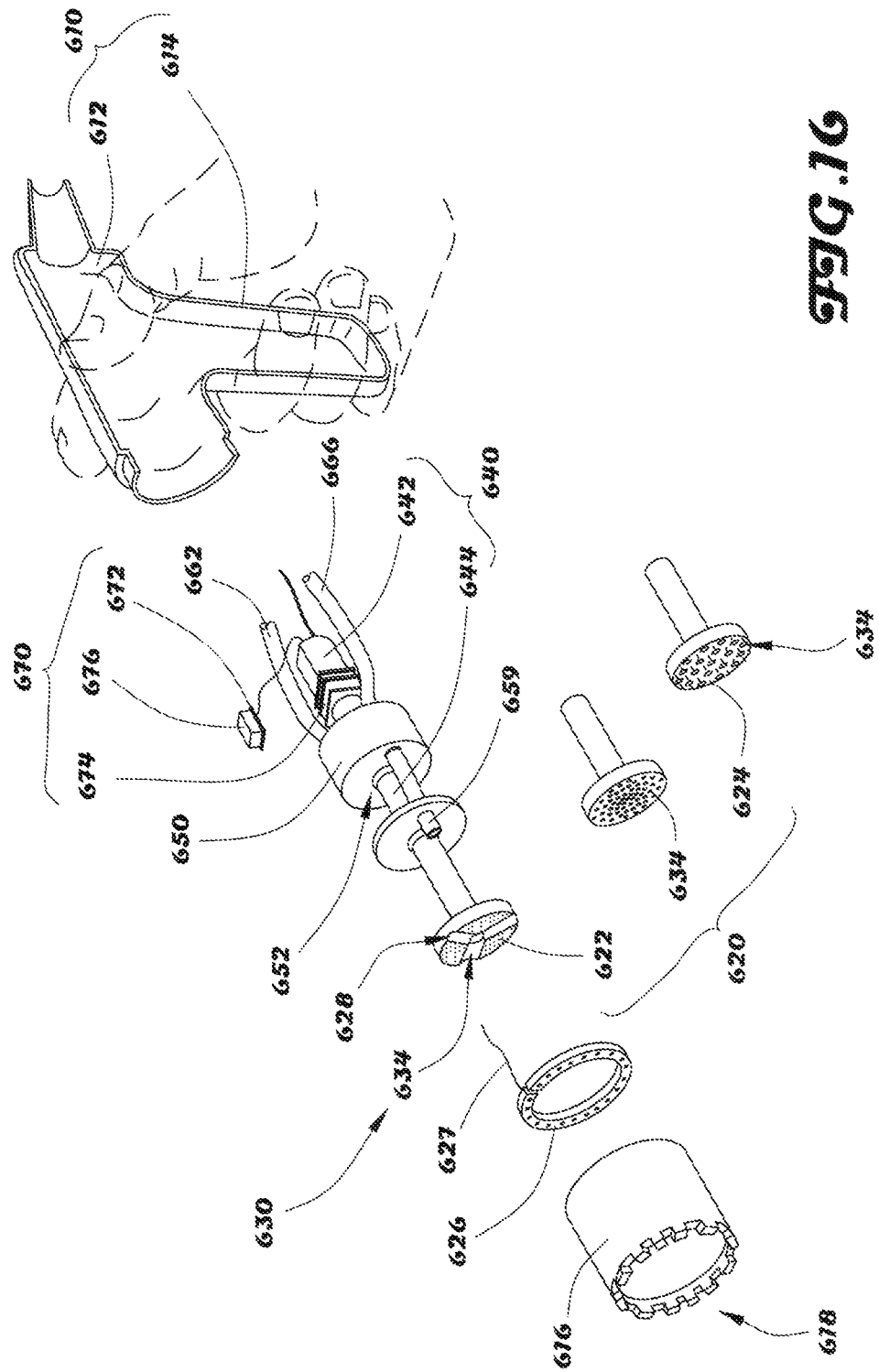

FIG. 16 shows an apparatus for transdermal fluid delivery according to another embodiment of the present invention.

Figure 17:
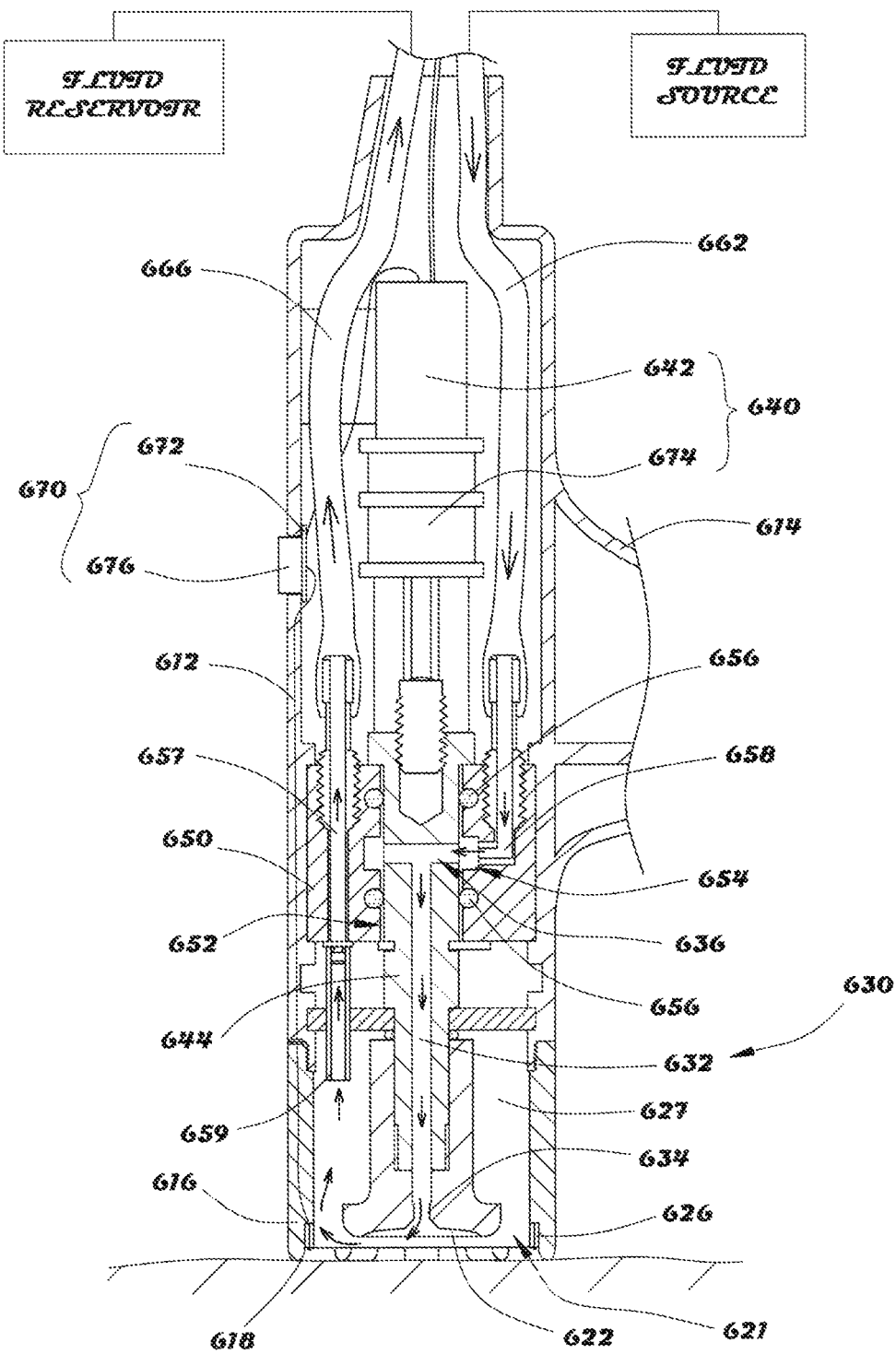

FIG. 17 is a sectional view of the apparatus in FIG. 16 according to another embodiment of the present invention.

Figure 18:
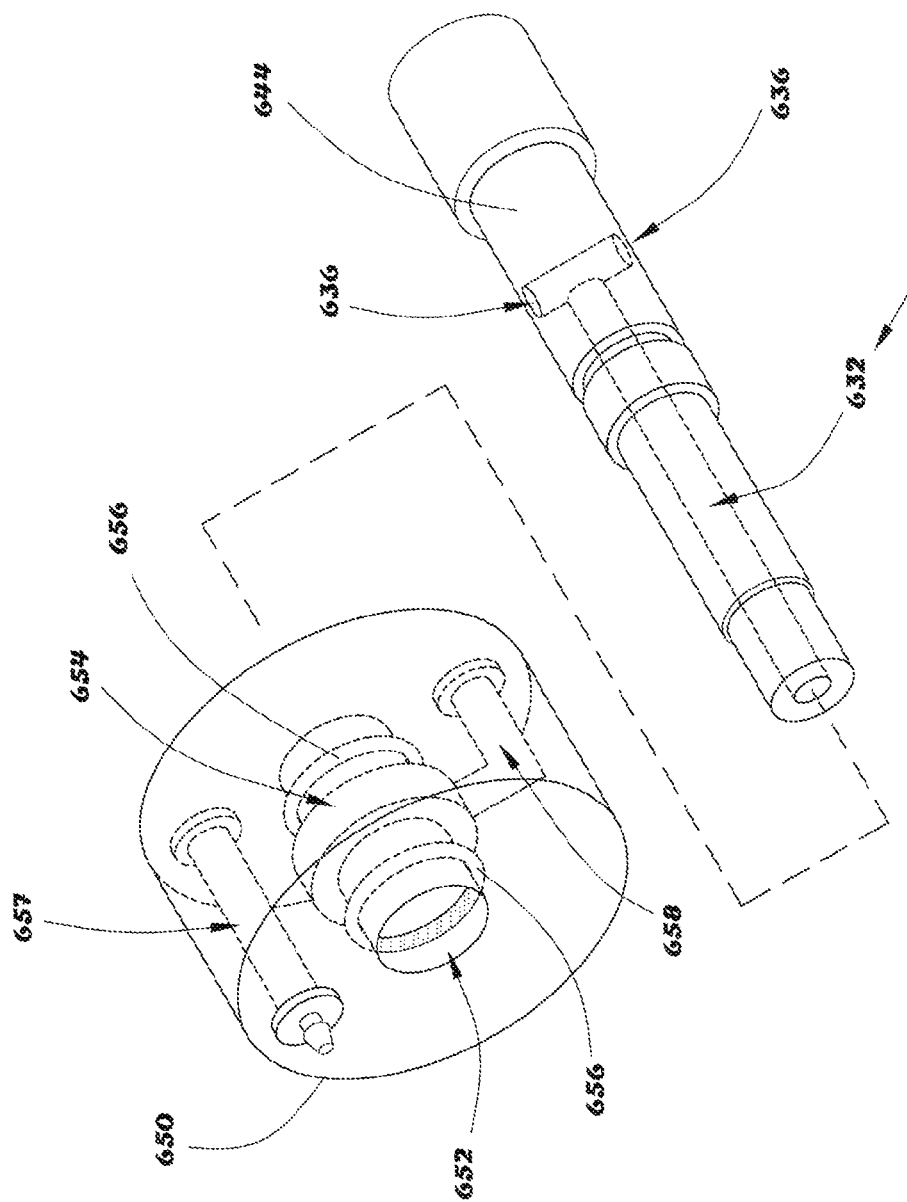

FIG. 18 is an exploded view of the driving shaft and the support member of the apparatus according to another embodiment of the present invention.

Figure 19:
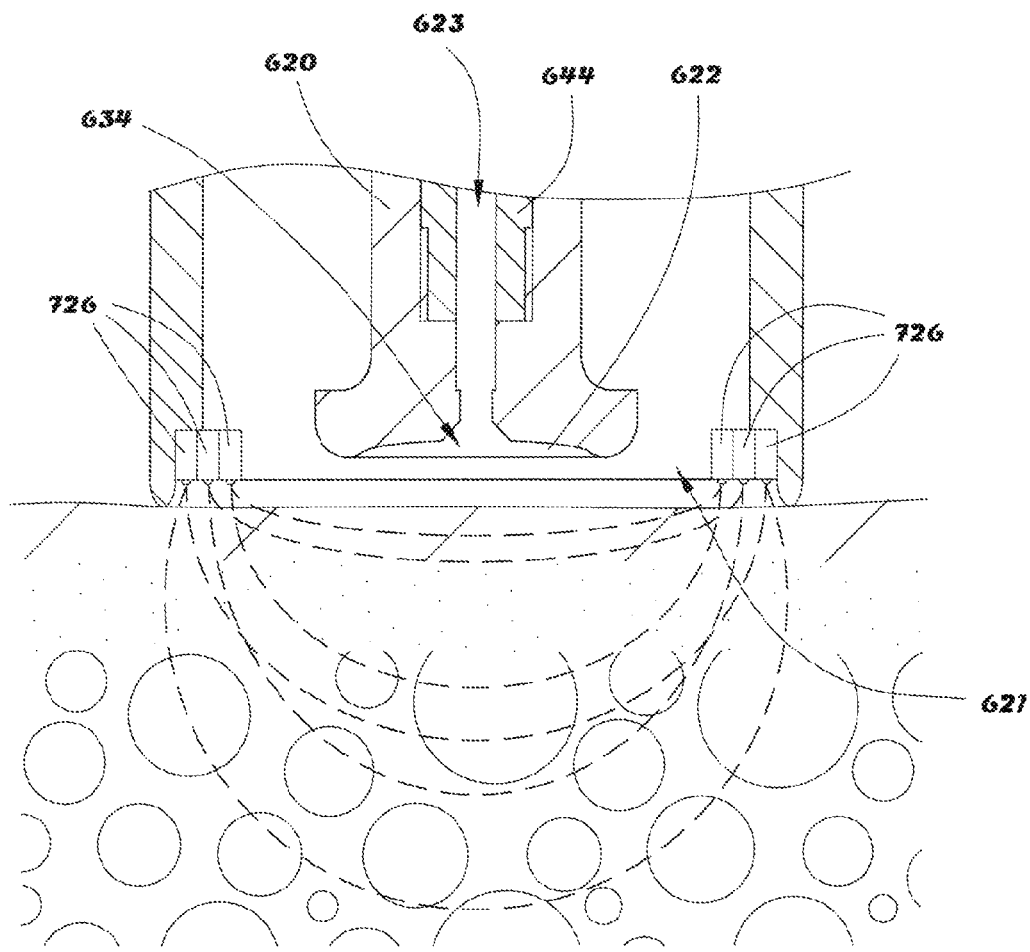

FIG. 19 shows a modification of the electrode module of the apparatus according to another embodiment of the present invention

DETAILED DESCRIPTION OF THE INVENTION

According to the present invention, a device, i.e. a microdermabrasion device, for increasing the permeability of the skins surface to fluid and/or drug delivery is described. In general, permeation of drugs and/or fluids through the skin occurs at a slow rate, if at all. The stratum corneum acts as a barrier that limits the penetration of substances through the skin. Application of high-voltage pulses to the skin increases its permeability (electroporation) and enables the delivery of various substances into and through the skin. The application of electroporation to the skin has been shown to increase transdermal drug delivery. Moreover, electroporation, used alone or in combination with other enhancement methods, expands the range of drugs (small to macromolecules, lipophilic or hydrophilic, charged or neutral molecules) that can be delivered transdermally. The efficacy of transport depends on the electrical parameters and the physicochemical properties of drugs. The in vivo application of high-voltage pulses is well tolerated.

According to one embodiment of the invention, a device comprising an abrading surface, fluid delivery, current delivery; and fluid vaccuation is described. The device enhances fluid delivery through the stratum corneum by first delivering an abrasive media to the surface of the skin to prepare the skin for fluid delivery. Next, the device delivers fluid to the surface of the skin, with simultaneous current delivery (electroporation). The combination of skin abrasion, followed by simultaneous fluid delivery with electroporation allows for deep penetration of fluid through the skin by increasing the skin's permeability. In addition to enhancing fluid delivery through the stratum corneum, the device resurfaces the outer surface of the skin, removing dead skin cells and the outer layer of dermis, along with other superficial imperfections. Unlike known microdermabrasion devices, the results achieved with the device of the present invention will have enhanced and longer lasting results, namely, because skin enhancing fluids and drugs are delivered more deeply into the skin with the simultaneous electrooporation, and the electrical induced therapy itself has skin enhancing properties, such as increased collagen production, muscle tone, and overall skin elasticity and firmness.

The device and methods described herein have an efficient fluid supply/return for transdermal/topical delivery of skin enhancing drugs and medicaments. This feature of the invention has been found to be particularly important since presently known technologies use a gel which is applied to the skin which limits the penetration of effective ingredients because of the greater molecular weight of the gel. Macromolecule delivery through a liquid, which can be accomplished with the present invention, is accordingly more effective than prior art technologies which use a gel. The application of an abrasive as described in this invention solves this issue of lowering the impedance of the stratum corneum thus further improving drug delivery to the skin. Accordingly, the device and methods of the present invention, which include fluid delivery with electro-current and a vacuum source, enable simultaneous application of fluids containing skin enhancing drugs, with increased topical delivery through an abrading surface, to achieve the maximum effect. The abrading surface, which is applied to the skin preferably prior to fluid/drug delivery, increases topical drug delivery and penetration of the drug to the lower layers of the skin. These features of the invention are an improvement over prior art technologies which lack a fluid delivery and a vacuum source and more particularly in combination with an abrading surface and electro-current application to accomplish skin resurfacing and enhancement.

As used in this disclosure, the term "comprise" and variations of the term, such as "comprising" and "comprises," are not intended to exclude other additives, components, integers or steps.

In one embodiment, the present invention is a device for enhancing fluid delivery to the skin. Referring now to FIG. 1A, a skin abrading device 100 having fluid and current delivery is shown. The device 100 comprises a handle 102, a tip 104, and a distal end 106. Positioned at the distal end are one or more conduits such as an electrical conduit 108, a fluid delivery conduit 110, and a vacuum conduit 112. The skin abrading device 100 may further include one or more switches for controlling the device 100 such as a switch 114 and/or 116 for controlling electrical current delivered via the electrical conduit 108, and/or control vacuum and/or fluid delivery from the fluid delivery and vacuum conduits 110 and 112. However, in other embodiments, these switches are positioned remotely on an adjunct device. The optional vacuum function of the evacuates fluid and skin debris from the surface of the skin and delivers the evacuated fluid and skin debris to an optional waste container (not shown) which may be positioned on the handle or in an adjunct device.

As shown in FIG. 1A, the handle 102 may be cylindrical with molded hand grip, or it may have other configurations such as cylindrical (without a molded hand grip), or other variations, including elliptical, square, rectangular, and variations thereof. The handle 102 may be formed of various materials as known to those in the art including any suitable plastic, metals, such as aluminum, stainless steel, and other alloys, and combinations of metal and plastic. Preferably, the handle 102 is made from a high density plastic material.

Referring now to FIG. 1B, a partial side cut-away view of the device 100 shown in FIG. 1 is shown. As shown in FIG. 1B, the handle 102 of the device 180 comprises an interior 118 and an outer casing 120. The fluid delivery conduit 110 is positioned in the interior 118 of the handle 102 and delivers fluid 120 from a reservoir (not shown) in an adjunct device through the fluid delivery conduit 110 and out the tip 104 of the device 100. The fluid 120 exits the tip 104 through a fluid delivery tip 122 having one or more apertures 124. Also positioned within the interior 118 of the handle 102 is the vacuum conduit 112 which pulls a vacuum from a vacuum pump (not shown) stationed in an adjunct device through the vacuum conduit 112. The vacuum conduit 12 has a vacuum entry port 126 positioned within the tip 104 for evacuating fluids and other debris from the surface of the skin. The interior 118 of the device 100 has one or more electrical conduits 108a, 108b, which deliver current either to an electronics board 128, which then delivers current to one or more electrodes 130, shown as 130a and 130b. Positioned within the tip 104 is an abrading structure 132 having an abrading end portion 134, which comprises an abrasive media 136. Within either the interior 118 of the device, electronic control circuitry 138 may be positioned for controlling current to the electrodes 130.

Referring now to FIGS. 2A, 2B, and 2C, preferred embodiments of the tip 104 of the device 100 are shown. As shown in FIG. 2A, the tip 104 may be somewhat tapered at the end, or in other embodiments, the tip 104 may be substantially cylindrically shaped or other, such as oval shaped, squared, or rectangularly shaped. As also shown in FIG. 2A, preferably, the fluid delivery tip 122 is domed shaped, having a plurality of apertures 124, such that a spray effect is achieved with the fluid delivery tip 122, (However, in other embodiments, the fluid delivery tip 122 may be flat, and/or have a single aperture 124. Multiple apertures 124 spread the liquid evenly along the area of the skin. Preferably, the fluid delivery tip 122 is positioned with respect to the tip 104, electrodes 130, and abrading structure 132 such that the fluid delivery tip extends slightly beyond or substantially flush with the abrading structure 132.

The tip 122 of the dome creates a planar surface of the skin preventing the vacuum suction from causing a subcutaneous hemotoma which is caused when the lining of blood vessels are damaged and blood escapes through the skin.

The vacuum entry port is positioned with respect to the tip 104, such that the vacuum entry port 126 minimizes skin trauma and ruptured capillaries, veins and arteries from the vacuum 124, yet creates a suitable vacuum to evacuate fluid and debris from the skin's surface. According to a preferred embodiment, the vacuum entry port 126 is positioned on the tip 104 such that when the tip 104 of the device 100 is applied to the surface of the skin, a space is created between the tip 104 and the vacuum entry port 126 to create a vacuum, known in the art as a closed loop system.

In a preferred embodiment, the fluid delivery tip 122 is substantially flush to the skin with respect to the abrading end portion 134 of the abrading structure 132 and the electrodes 130 such that when the device 100 is applied to the skin, the skin stays relatively flat during treatment. According to this embodiment, when the abrasive media 136, vacuum 124, fluid 120, and electric current 140 are applied to the skin with the configuration described with respect to this embodiment, having the various structures of the tip 104 substantially flush to the skin minimizes the possibility of skin trauma associated with the pulling up of skin in a space of vacuum 124.

In an alternate embodiment, the vacuum entry port 126 can be positioned in other portions of the tip 104 to provide an optimal vacuum of concurrent liquid delivery and/or removal of skin debris. However, the vacuum entry port 126 is preferably positioned to keep a higher level of fluid within the tip of the handle during treatment so as to have a higher absorption and penetration rate of ingredients contained in the fluid, into the skin, while still evacuating skin debris and preventing the fluid 120 from flowing away from the desired treatment area and/or falling off the skin.

The abrading structure 132 is positioned with respect to the tip 104, such that the abrading end portion 134 of the abrading structure 132 is substantially flush to the surface of the skin, in other embodiments, the abrading structure 132 may be lowered or raised with respect to the end of the tip 104 to provide skin contact, as desired by the user.

In a preferred embodiment, the abrading, structure 132 has a range of abrasiveness on the abrasive media 136 from a substantially smooth surface (no abrasion) to very abrasive depending on the treatment type. As shown in FIGS. 1B, and 2A-2B, the abrading structure 132 is positioned on the outer edge of both a fluid supply, i.e., the fluid delivery tip 122 and vacuum port 126 and on the inside of the electrodes 130. However, according to the present invention, other arrangements of the abrading structure 132, electrodes 130, and fluid delivery tip 122 and vacuum port 126 are possible, as will be understood by those of skill in the art.

The abrading structure 132 may be reusable or disposable, in part or entirely. For example, according to one embodiment, the abrading end portion 134 and the abrasive media 136 are integral to the abrading structure 132. According to this embodiment, the abrading structure may be reusable or disposable in part or entirely. When the abrading structure 132 is reusable, it is preferably designed to be sanitized and cleaned between uses and reused. In an alternate embodiment, the abrasive media 136 is positioned on the abrading end portion 134 in a removable fashion, such as a removable strip. According to this embodiment, the abrading structure 132 is generally reusable and the abrasive media 136 on the abrading end portion 134 is preferably disposable.

The abrasive media 136 comprises a material suitable to abrade the surface of the skin such as sand paper, rough textiles (such as dermal grade fabrics that are used in cosmetic microdermabrasion, typically made from 100% medical grade nylon and have a plurality of coatings and finishes), wire brushes, carbon fibers, and microneedles. The material can be conductive or non-conductive. According to one embodiment, the abrasive media 136 comprises a non-conductive sand paper. In one embodiment, the sand paper is white aluminum oxide, a non-conductive material, readily available at low cost in medical grade. This material is able to withstand elevated temperatures, such as those typically present in any vitrification process that may be necessary for high volume binding/fabrication to produce the abrasive tip. According to other embodiments, a material softer than aluminum oxide is preferred so that the material is less irritating to the skin than aluminum oxide. According to this embodiment, the abrading media 136 comprises polymeric beads. Generally, polymeric beads provide a softer, less irritating material than aluminum oxide. However, other materials according to the invention may be used as the abrading media 136, where the material is selected based on the particular individual to be treated and the purpose of the treatment. Accordingly, for different individuals, different materials may be substituted for the above-listed materials. In other embodiments, the abrasive media 136 comprises a conductive material. Suitable conductive materials include, but are not limited to, metals, carbon, conductive polymers and conductive elastomers.

The abrading end portion 134 may have a variety of suitable thicknesses and diameters. According to one embodiment, abrasive particles are coated onto the abrading end portion of the abrading structure 132. In some embodiments, the abrading structure 132 and abrading end portion 134 comprise a unitary plastic structure, such as acrylonitrile butadiene styrene (ABS). According to this embodiment, the abrasive media is an abrasive coating adhered to the abrading end portion 132, or the abrasive media 136 is of a unitary construction with the abrading structure 132 and abrading end portion 134. According to one embodiment, the abrasive media comprises abrasive particles which are adhered to the abrading end portion 134, where the thickness of the abrasive media 136 is defined by the grit size of the abrasive particles. According to this embodiment, the abrasive particles are generally of a size ranging from about 300 to 50 grit (about 50 to 300 microns), and typically about 100 to 120 grit and may comprise carborundum (aluminum oxide), sodium bicarbonate, polymeric particles, and the like. Coarser particles (at the lower ends of the grit ranges (about 35 to 50, and typically less than 100) may also be provided for use in initial treatments, or treatments on coarser areas of the skin (such as arms), while finer particles (at the higher ends of the grit ranges about 300 and above) may be employed for subsequent treatments. Alternately, the abrading end portion 134 may be formed by knurling, machining, laser treatment or otherwise mechanically or chemically treating the end of the abrading end portion 134 to provide an integral abrasive media 136 which has a unitary construction with the abrading end portion and abrading end structure 132. In a preferred embodiment, the abrasive media 136 is abrasive particles having a grit size of about 120 or lower (approximately 0.0044 inches in diameter).

Typically the abrading end portion 134 will have a thickness ranging from 0.5 microns to 150 microns, preferably ranging from 15 microns to 120 microns. The diameter of the abrading end portion 134 is variable depending on the type of application. For example, in applications having a small area to be permeabilized, the abrading end portion 134 can have a diameter of up to several micrometers, such as from 1 to 25 microns. For applications having a larger area to be permeabilized, the abrading end portion 134 can have a diameter of up to several inches, such as from 0.1 to 5 inches (2.5 mm to 127 mm).

According to the present invention, a current 140 (not shown) is delivered from the device 100 to the surface of the skin through one or more electrodes 130. The electrodes 130 can be a single electrode, or a plurality of nodes or combination thereof and may further have a variety of configurations and dimensions, such as nodes, bars, etc., as will be understood by those of skill the art.

Electrical currents, known for application to the skin, which may be used according to the present invention include:

a. Electroporation. Electroporation refers to the application of electric pulses to increase the permeability of cell membranes. According to the present invention, electric pulses are applied to skin cells to increase membrane permeability.

b. Microcurrent. Microcurrent refers to the application of a small current used in a noninvasive electrotherapy technique where electrodes are applied at acupuncture points. In general, 10-500 microamps (Ua) are applied to the surface of the skin and for optimal effectiveness, the current applied to the skin should not cause an actual "visual" contraction of the facial muscles. In some applications, electroporation refers to the process of applying a microcurrent to the surface of the skin.

c. Iontophoresis. Iontophoresis refers to a therapeutic type of transcutaneous drug delivery in which electric current is applied to the skin to enhance absorption of large polar or hydrophilic molecules and peptides—e.g., insulin, and control therapeutic delivery. According to the present invention, a galvanic current is applied an ionizable agent in contact with a surface of the skin, by means of an appropriate electrode, to hasten the movement into the tissue of the ion of opposite charge to that of the electrode. Accordingly, skin enhancing agents which are polar or hydrophilic may be delivered into the skin.

d. Sonophoresis. Sonophoresis refers to a process that exponentially increases the absorption of semisolid topical compounds (transdermal delivery) into the epidermis, dermis and skin appendages. Sonophoresis occurs where ultrasound waves stimulate micro-vibrations within the skin epidermis and increase the overall kinetic energy of molecules making up topical agents. Skin enhancing agents may be mixed with a coupling agent (gel, cream, ointment) to transfer ultrasonic energy from the ultrasound transducer (i.e., electrode) to the skin and enhancing drug transport through the skin.

e. Galvanic. Galvanic or Galvanic current refers to the current which is the electrical current used in the process of Iontophoresis.

f. Ultrasound. Ultrasound or ultrasonic current refers to the current used in Sonophoresis. Ultrasound is cyclic sound pressure with a frequency greater than the upper limit of human hearing. Although this limit varies from person to person, it is approximately 20 kilohertz (20,000 hertz) in healthy, young adults and thus, 20 kHz serves as a useful lower limit in describing the ultrasonic current applied via the electrodes in the present invention.

g. Ultrasonic Cavitation. Ultrasonic Cavitation refers to an advanced ultrasonic machine having 3 MHz and 1 MHz ultrasound frequencies for the body and a 1.4 MHz ultrasonic frequency for the face, and an ultrasonic cavitation wavelength at 47 KHz. In Ultrasonic Cavitation, the ultrasonic waves are able to act on the skin surface (3 MHZ ultrasound), providing skin tightening as well in the deep layers, (cavitation) providing real results, after the treatment, in terms of cellulite and localized adiposity. It has been shown to be able to eliminate centimetres of belly, buttocks, hips and thighs without any side effects. Ultrasonic waves in a specific range from 20 to 70 KHz are able to cause the "cavitation" effect: focused high energy waves which creates micro bubbles of vapor inside the adiposities and in the interstitial liquids of cellulite.

h. Acoustic cavitation. Acoustic Cavitation refers to a non-flowing system where the ambient pressure can be varied by sending sound waves through a liquid. The ultrasonic sound waves are made up of alternate compressions and rarefactions. During the rarefaction cycle (low pressure) a lot of microscopic bubbles will grow and during the compression cycle (high pressure) each bubbles undergoes a collapse or implosion.

i. Mesotherapy. Mesotherapy refers to a procedure in which multiple tiny injections of pharmaceuticals, vitamins, etc., are delivered into the mesodermal layer of tissue under the skin, to promote the loss of fat or cellulite.

J. Radio Frequency. Refers to a procedure using a beam of radio frequency energy to target deeper layers of the skin by heating them up. This creates stimulation of the skin and in particular, the collagen, a substance which gives elasticity to the skin. The radio frequencies cause water molecules in the deeper layers of skin to vibrate. This in turn creates friction which causes the heating effect. When heat is applied to collagen fibres, they shrink and tighten up, and over time following the treatment, new collagen also forms.

k. Not and cold therapies. Refers to using an electrical current and other modalities to create different adjustable temperatures ranging from hot (up to 140 degrees Fahrenheit) to cold (down to 5 degrees Fahrenheit) to treat the surface layer skin by softening and/or tightening collagen fibers.

In a preferred embodiment of the present invention, a microcurrent is applied to the skin, i.e., electroporation. According to this embodiment, the current of the device 100 is set for a wave form with power between 10-500 microamps (Ua). The current 140 (not shown) is delivered through the device 100 and through one or more electrodes 130 to the surface of the skin. Treatment can be substantially stationary in certain areas, or vary in the degree of motion, up to sweeping lines.

According to another embodiment, a combination of two or more frequencies of current are applied from the device 100 to a patient. Accordingly, in some embodiments the device is capable of delivering a plurality of different frequencies (i.e., types) of current, either individual applied or concurrent. For example, an ultrasonic current may be applied from the device 100 to a patient, followed by delivery of a microcurrent from the device 100 to the same patient. The treatment may be in one treatment area, or over a plurality of treatment areas, such the delivery of microcurrent to the face, followed by delivery of ultrasonic current to the arms. The plurality of frequencies may be used on one patient for application of different electric currents. For example, ultrasound and microcurrent have different ways of penetrating fluids and treating the skin. The concurrent combination of these and other electric modalities shown in device 100 is to provide a more effective treatment.

Referring again to FIG. 1B, fluid 120 is delivered from a fluid reservoir (not shown), which may be either part of the handle or in a separate reservoir, such as a plastic or glass tube serum, through the fluid delivery conduit 108 and out the fluid delivery tip 122 in the tip 104 of the device 100. Fluid delivery may be used in the device for cleaning of the skin, as a vehicle for delivery of a therapeutic agent, or it may be the therapeutic agent itself, and/or the fluid may be an ionic agent to facilitate delivery of current 140 through the electrodes 130. The fluid may include one or a plurality of suitable skin enhancing agents, and/or conductive ingredients, or other suitable agents for skin cleaning and skin enhancement or facilitation of current delivery, such as water, salts, ionic or non-ionic surfactants, preservatives, alcohol, glycerol, gel, and other similar agents. Various mixtures of these agents may be formulated into fluids with various conductivity levels, depending on the desired application. Preferably, at least one of the fluids used in a method according to the present invention is a "highly conductive fluid" or a "fluid with a high conductivity" meaning a fluid with a conductivity from about 1,000 to about 100,000 (μSiemens/cm) to facilitate current delivery. Other fluids, such as a "fluid with a low conductivity", meaning a fluid with a conductivity from about 0.1 to about 999 (μSiemens/cm), are used according to the invention in other applications, such as cleaning, and/or delivery of a skin enhancing or therapeutic agent. A highly conductive fluid is used according to the present invention to provide a conductive path through the skin, in a preferred embodiment, at least one fluid with a conductivity of at least 500 to about 50,000 uSiemens/cm is used.

Therapeutic or skin enhancing fluids useful in the device 100 according to the present invention may be of a variety of therapeutic agents. For example, the fluid may be a skin treatment liquid, a lotion liquid, and/or a vitamin liquid, or a combination thereof. The fluid may also be a pharmacologically-active agent, where the fluid carries a chemical agent of a suitable concentration. Examples of such agents include TCA (trichioroacetic acid), a glycolic acid including an alphahydroxy acid (AHA), a lactic acid, a citric acid, and phenol, alone or in combination with other agents or fluids. Examples of other therapeutic or skin enhancing agents include type A botulinum toxine, phosphatidylcoline, aminophylline, hyaluronic acid, L-carnitine, vitamins, amino acids, collagen, lidocaine, heparin, elastine, compounds for Mesotherapy procedures, glutathione, hormone replacement agents, hyaluronidase, MTE-4 (Copper-Manganese-Zinc Sulphate-Chromium), ionic skin tissue growth gels, enzymes, peptides and steroids.

Other ingredients can include plant and fruit derived ingredients, such as enzymes and stem cells derived from fruits and/or plants, etc. Since microdermabrasion is a controlled injury of the skin by abrading the surface layer to cause a wound healing response, other known healing and anti-inflammatory ingredients such as cortisone, aloe extract, etc. may be used to increase healing response time and also act as an anti-fungal, anti-viral, anti-bacterial and acaricidal activity against skin infections such as acne, etc, may be used individually or in any combination with other sterile fluids, drugs, and other skin enhancing and/or therapeutic agents.

Other agents and preferred viscosity parameters may be found in "Advanced drug delivery reviews", 56 (2004) 659-674, Referring again to FIG. 1B, a vacuum 124 may be applied to the surface of the skin from a vacuum pump (not shown) through the vacuum conduit 112 and vacuum entry port 126 on the tip 104 of the device. Preferably, the vacuum pump which supplies the vacuum 124 to the device 100 has a rating of 2.9A, with a max flow rate of 2 cu.ft/min, a power rating of 120 W, with a 60 Hz frequency, and preferably RoHS compliant, although other embodiments are possible. In general, the vacuum 124, used during a treatment and applied to the surface (or just above) the skin of a patient, is a continuous flow and preferably can be adjusted with a flow control valve to increase or decrease vacuum pressure.

Referring now to FIG. 3A, a skin abrading device 100, having a plurality of removable, exchangeable, and attachable tips, according to a preferred embodiment of the invention is shown. As shown in FIG. 3A, the tip 104 of the device 100 comprises multiple nesting (e.g., interconnected) structures which are removable/attachable from the handle 102. The outer structure 142 of the tip 104 comprises the electrodes 130 at the proximal end of the tip 104 and wiring (not shown) for delivering current 140 (not shown) to the electrodes 130. Positioned within the outer structure 142, is the intermediate structure 144, which is also the abrading structure 132. The inner structure 146 comprises the fluid delivery tip 122 and vacuum entry port 126. When the structures 142, 144, and 146 (i.e., tips) are assembled, the tip 104 of the device 100 will have the configuration shown in FIGS. 1A, 1B, and 2A-2C.

That is to say, the inner structure 146 is located at the center of the tip. The outer structure 142 is located at the periphery of the tip. The intermediate structure 144 is located between the inner structure 146 and the outer structure 142. The outer structure 142, intermediate structure 144, and the inner structure 146 are coaxial with each other and are in a ring shape. Preferably, the outer structure 142 and intermediate structure 144 form an outer ring and intermediate ring respectively at the tip. The outer ring and intermediate ring can be formed in a circular shape or a non-circular shape. Therefore, the abrading end portion forms at the intermediate ring and encircles the fluid delivery tip 122 and vacuum entry port 126 of the fluid delivery. The electrodes 130 are aligned at the outer ring to encircle the abrading end portion at the intermediate ring.

The outer structure 142, intermediate structure 144 and inner structure 146 are connected to the handle 102 with a suitable connection, such as compression fitting, threaded fittings, etc. In a preferred embodiment, one or more of the outer structure 142, intermediate structure 144, and inner structure comprise stainless steel. In one preferred embodiment, the intermediate structure 144 comprises a reusable stainless steel abrading structure 132 having an abrading end portion 134 which has a diamond coated abrasive as the abrasive media 136. In another preferred embodiment, the intermediate structure 144 comprises a disposable (preferably translucent) plastic abrading structure 132 having a disposable abrasive media 136 positioned on the abrading end portion 134. In another preferred embodiment, the inner structure, comprising the fluid delivery tip 122 and the vacuum entry port 126, are one or more of transparent, detachable, and/or disposable. Although the outer structure 142, intermediate structure 144, and inner structure 146 have been described herein as removable, exchangeable, and attachable, it will be understood by those of skill in the art that one or more of the outer structure 142, intermediate structure 144, and inner structure 146 may be affixed to the handle 102 in a permanent, or not-easily removable fashion. However, in other embodiments, one or all of the structures 142-144 may be one piece in any arrangement or separate individual connections. For example, the device may comprise a handle 102 with an electric current node (i.e., electrode 130) in the middle surrounded by a fluid delivery piece 122 and an abrasive structure 132 making the outer edge of the handle. This is just an opposite arrangement from the arrangement shown in FIG. 3A, and as it will be understood by those of skill in the art, interrelationship of the various tips shown in the Figures is by way of example and other configurations are within the scope of the invention.

Referring now to FIG. 3B, another embodiment of the abrading structure 132 is shown. According to this embodiment, the abrading end portion 134 of the abrading structure 132 comprises one or more grooves 135. The grooves 135 may be differently shaped, such as rounded grooves, or slotted squares. The grooves 135 are provided to abrade the skin more effectively by stretching it, and to better guide skin debris into the vacuum. Preferably, to keep the vacuum 124 sealed, the grooves 135 are substantially even with the edge such that when the abrading structure 132 is applied to the skin, air does not escape. The grooves 135 may have a variety of thickness or radius, shape or design, for different skin types and applications, as will be understood by those of skill in the art. According to this embodiment, extraction can be realized by pressing the abrading end portion 134 and grooves 135 to the skin, such that the grooves 135 act as a comedone extractor on a pore. For example, when the abrading end portion 134 having grooves 135 is pressed to the skin, oil and sebum will be released from the pores.

Referring now to FIG. 4, a partial side cut-away view of the device 100 having a wide-angle tip 104 is shown. As shown in FIG. 4, the same numbers refer to the same features shown in FIG. 16, with the differences noted below. According to this embodiment, the tip 104 of the device is a wide angle tip, where the fluid 120 exits the tip 104 through a fluid delivery tip 122 having a plurality of apertures 124a-124d. According to this embodiment, the wide angle tip allows for an increased area for fluid delivery and more apertures for fluid delivery. The interior 118 of the device 100 has one or more electrical conduits 108a, 108b, which deliver current either to an electronics board 128, which then delivers current to one or more electrodes 130, or directly to the electrodes. As the tip 104 is a wide-angle tip, the electrodes are positioned further from the center of the tip 104 and in some embodiments, this allows for additional or wider electrodes 130 than the tapered tip 104 shown in FIG. 1A and FIG. 16. Positioned within the wide angle tip 104 is an abrading structure 132 having an abrading end portion 134, which comprises an abrasive media 136. Similarly to the electrodes 108, the abrading end portion 124 and abrading media 132 are positioned further from the center of the device than the tapered tip 104 shown in FIG. 1A and FIG. 16. This embodiment may be used on a treatment area with a larger surface area that can accommodate the larger tip surface area. The various tips comprising the outer structure 142, intermediate structure 144, and inner structure 146, shown in FIG. 4, may be removable, exchangeable, and attachable, and may be exchanged with other interchangeable tips 142-144, of other dimensions, as described herein.

Referring now to FIG. 5A, a skin abrading device 100, having a plurality of removable, exchangeable, and attachable tips, according to another preferred embodiment of the invention is shown. Unless otherwise noted below, the same reference numbers refer to the same elements as described with reference to FIG. 3. As shown in FIG. 5A, the tip 104 of the device 100 comprises multiple nesting (e.g., interconnected) structures which are removable/attachable from the handle 102. As shown in FIG. 5A, the electrodes 130a and 130b are concentric circles positioned within the outer structure 144 of the tip 104. Positioned within the outer structure 144, is the intermediate structure 144, which is also the abrading structure 132. The inner structure 140 comprises the fluid delivery tip 122 and vacuum entry port 126. Referring now to FIG. 5B, a partial side cut-away view of the device 100 shown in FIG. 5A, having electrodes 108a, 108b, which are concentric circles is shown. When the structures 142, 144, and 146 (i.e., tips) are assembled, the tip 104 of the device 100 will have the configuration shown in Figure SB. The outer structure 142, intermediate structure 144 and inner structure 146 are connected to the handle 102 with a suitable connection, such as compression fitting, threaded fittings, etc. As shown in FIGS. 5A and 5B, the tip 104 is substantially linear with respect to the handle. However, in other embodiments, the tip 104 may be tapered as shown in FIG. 1A or wide angled, as shown in FIG. 4. The structures 142-146 may comprise any suitable metal such as stainless steel, or may be any suitable plastic that is transparent, detachable, and/or disposable, and may be removable, etc, as shown in FIG. 5A, or substantially fixed, as described herein with respect to other embodiments, as will be understood by those of skill in the art.

Although the electrodes 130, shown in FIG. 5A and other Figures, are shown as positioned on the outer structure 144, the electrodes 130 may be positioned on the inner structure 146 and the fluid delivery portion 122 and/or the abrasive portion 132 may be positioned in the outer and intermediate structures 142 and 144, in a variety of combinations, either removable/attachable or permanently part of the handle, as will be understood by those of skill in the art.)

FIG. 6A shows an alternate embodiment of the skin abrading device 100 according to another embodiment of the present invention. As shown in Figure SA, the device 100 has a divided handle 102a and 102b. FIG. 6B is a cross sectional view showing the divided handle 102a and 102b of Figure BA. As shown in FIG. 6B, the top portion of the handle 102a comprises the fluid delivery conduit 110 and the vacuum conduit 112 and the bottom portion of the handle 102b comprises the electrical conduits 108a. The tip 104 of the device 100 shown in FIG. 6B, may have one or all of the configurations disclosed herein, including removable/interchangeable outer, intermediate and inner structures 142, 144 and 146 for the tip 104 portion of the device 100, as shown in FIGS. 3-5.

As shown in FIGS. 1-6, each of the embodiments described comprises tip 104 having electrodes 130, an abrading structure 132, and fluid delivery 122. However in other embodiments, the device may have only two of these features, such as the combination of electrodes 130 and fluid delivery 122, without the electrode 130 feature, as will be understood by those of skill in the art.

According to another embodiment, a method for treating a skin surface of a patient is provided. According to the method, a device according to the invention is employed to abrade the skin surface of a patient; deliver fluid to the surface of the skin; and apply current to the surface of the skin. These steps may be performed in the sequence described herein, or the sequence may be altered, depending on the type of procedures to be performed on the patient, as will be understood by those of skill in the art.

In a preferred embodiment, first the abrading end portion 134 of the abrading structure 132 of the device 100 is applied to the skin surface of a patient. Vacuum may optionally be applied to the skin surface to remove any residual debris, such as abrasive media and excess skin, either after or during the abrading portion of the treatment. Then, the skin surface is contacted with the abrading end portion 134 and abrasive media 136 of the device and the abrading end portion 134 of the device 100 is moved over the surface of the skin. Treatment can be substantially stationary in certain areas, or vary in the degree of motion, up to sweeping lines. Next, a fluid is provided to the skin surface through the fluid delivery tip 122 of the device 100. Then, a current 140 is applied to the surface of the skin by transferring current from the electrodes 130 to the skin surface. The current 140 may be applied either to wet or dry skin.

Although the method is described above as being performed in a sequential manner, this is provided by way of example, and is only one of the possible protocols for the method of the invention. Accordingly, according to the method of the invention the various treatments, including skin abrasion, fluid delivery, and/or current delivery may be performed concurrently, or one at a time, in any order, depending on the patient needs and treatment given to any particular patient.

Another embodiment in FIGS. 7 to 9 illustrates a modification of the tip 204 that detachably couples to the handle 102. The tip 204 is a multi-functional tip to provide multiple functions. The tip 204 has a slanted skin applying surface, wherein the outer structure 242, intermediate structure 244, and the inner structure 246 are coaxial with each other and are formed at the slanted skin applying surface with respect to the handle 102. The skin applying surface is a flat surface.

The outer structure 242 of the tip 204 comprises the abrading structure 232, wherein the abrading end portion 234 of the abrading structure 232 comprises one or more abrading edges 236a, 236b. The abrading structure forms an abrasive crown. In FIG. 7, the abrading structure 232 comprises an inner abrading edge 236a and an outer abrading edge 236b, wherein the inner abrading edge 236a and outer abrading edge 236b form in a ring shape, which can be a non-circular ring, shape or a circular ring shape. The abrading end portion 234 of the abrading structure 232 comprises a plurality of connecting abrading edges 236c spaced apart with each other and extended between the inner abrading edge 236a and outer abrading edge 236b to form a crown shaped abrading structure. A plurality of grooves 235 are formed between every two of the connecting abrading edges 236c. The grooves 235 may be differently shaped, such as rounded grooves, or slotted squares. The grooves 135 are provided to abrade the skin more effectively by stretching it, and to better guide skin debris into the vacuum. Of course, the abrasive media 236 can also be replaceably placed at the abrading end portion 234 of the abrading structure 232 between the inner abrading edge 236a and outer abrading edge 236b.

The intermediate structure 244 comprises the electrodes 230 arranged in a ring shape. At least one electrode ring 231 is provided, wherein the electrodes 230 are spacedly formed at the electrode ring 231. In FIG. 7, two electrode rings 231, i.e. inner and outer electrode rings, are provided, wherein the outer electrode ring 231 is encircled within the inner abrading edge 236a and the inner electrode ring 231 is encircled within the outer electrode ring 231. Each electrode ring 231 can provide at least one of operations of electroporation, microcurrent, iontophoresis, sonophoresis, galvanic, ultrasound, ultrasonic cavitation, acoustic cavitation, mesotherapy, radio frequency, and/or hot and cold therapies. The two electrode rings 231 can provide two different operations respectively. Therefore, two different sets of electrodes 230 are provided at the inner and outer electrode rings 231 respectively. For example, one of the electrode rings 231 is to produce an electrical stimulant function, and another electrode ring 231 is to produce heat.

It would be acceptable that one single electrode ring 231 is replaceably formed at the intermediate structure 244 as shown in FIG. 10. The single electrode ring 231 can be a sonic brush tip in FIG. 10.

Each of the electrode rings 231 is replaceable, detachable, and/or disposable. Each electrode ring 231 has a latch 231a extended from the electrode ring 231, wherein the latch 231a is slot-in the latch slot 232a at the sidewall of the tip 204 to detachably couple the electrode ring 213 at the slanted skin applying surface of the tip 204. The electrode rings 231 are attached to the removable tip and can provide multiple frequencies.

A terminal 239 is provided at the handle 102 and is electrically linked to the control circuit 138. When the tip 204 couples to the handle 102, the electrodes 230 at the intermediate structure 244 will electrically contact and connect with the terminal 239.

The inner structure 246 comprises a fluid delivery structure, wherein the fluid delivery structure comprises the fluid delivery tip 222 and vacuum entry port 226. The fluid delivery tip 222 has at least one aperture 224, wherein the aperture 224 is formed at the slanted skin applying surface of the tip 204.

The vacuum entry port 226 is also formed at the slanted skin applying surface of the tip 204 and is located away from the aperture 224.

The intermediate structure 244 comprises the fluid electrode terminal 233 extended toward the aperture 224 to electrify the fluid when the fluid is ejected right at the aperture 244.

The inner structure 246 further comprises a plurality of fluid delivery walls 245 extended between the aperture 224 and the vacuum entry port 226 to form a fluid detouring path. When the fluid is ejected from the aperture 224, the fluid is guided and detoured along the fluid detouring path to the vacuum entry port 226. Therefore, the fluid detouring path will prolong the traveling distance of the fluid from the aperture 224 to the vacuum entry port 226.

In FIG. 7, two fluid delivery walls 245 are extended from two opposite sides, i.e. first and second sides, of a boundary wall that partitions the inner structure 246 into two side sections and a mid section. The boundary wall is the boundary of the inner structure 246. Therefore, the boundary wall is the wall between the inner structure 246 and the intermediate structure 244. One of the fluid delivery walls 245 is extended from the first side of the boundary wall toward the second side thereof to form a first cornering region. Another fluid delivery wall 245 is extended from the second side of the boundary wall toward the first side thereof to form a second cornering region. The aperture 224 and the vacuum entry port 226 are formed at the two side sections and are located at two ends of the fluid detouring path. Therefore, the fluid will travel from one side section to another side section through the mid section, wherein the fluid will pass the first and second cornering regions. Preferably, the fluid delivery walls 245 are extended in parallel. Therefore, the fluid detouring path is a zigzag path that the fluid travels in a zigzag manner from the aperture 224 to the vacuum entry port 226.

An additional vacuum entry port 226a is provided at the fluid detouring path between the aperture 224 and the vacuum entry port 226. The size of the additional vacuum entry port 226a is smaller than the size of the vacuum entry port 226. The additional vacuum entry port 226a will pull a small amount of fluid first before the vacuum entry port 226 pulls the rest of fluid. Preferably, the additional vacuum entry port 226a is located right after the second cornering region.

In the preferred embodiment, the outer structure 242, intermediate structure 244, and the inner structure 246 are integrated with the tip 204 at the skin applying surface. Only the electrode rings 231 are replaceably attached to the intermediate structure 244. The abrasive media 236 is optionally placed at the outer structure 242. Without the abrasive media 236, the inner abrading edge 236a, outer abrading edge 236b, and connecting abrading edges 236c at the outer structure 242 can perform the abrading operation.

The device of the present invention basically uses the electric current to stimulate blood circulation to increase the absorption of the liquid, similar to how the skin absorbs more when exercising or sweating from heat, the pores become more permeable. The electric currents to be used do cause the similar effect of softening the pores to allow liquid to penetrate deeper under the skin.

FIG. 11 shows the alternative of the tip 204 that has a slanted skin applying surface; wherein the inner structure 246, including the aperture 224, vacuum entry port 226 and fluid detouring path, remains the same. Only the outer structure 242 and intermediate structure 244 are interchanged. The electrode ring 231 is formed at the outer structure 242 and the abrading structure 232 is formed at the intermediate structure 244.

FIG. 12 shows another alternative of the tip 204. The inner structure 246, including the aperture 224, vacuum entry port 226 and fluid detouring path, remains the same. The electrode ring 231 is formed at the outer structure 242. The abrading structure 232 is formed at the intermediate structure 244. The modification in FIG. 12 is that the abrasive media 236 is placed at the abrading end portion 234 and is placed at the top surfaces of fluid delivery walls 245 to increase the abrading surface of the tip 204.

Another embodiment in FIG. 13 illustrates a modification of the tip 304 that detachably couples to the handle 102. The tip 304 is an electrode skin treating tip which comprises an electrode film 304a provided at the slanted skin applying surface for generating a specific electrical current such as of electroporation, microcurrent, iontophoresis, sonophoresis, galvanic, ultrasound, ultrasonic cavitation, acoustic cavitation, mesotherapy, radio frequency, and/or hot and cold therapies. The electrode film 304a can also be a light film for generating a specific light wave for skin treatment. The electrode skin treating tip 304 can be attached to the handle 102 after the multi-functional tip 204 is removed. Therefore, the multi-functional tip 204 and the electrode skin treating tip 304 are interchangeable. It is worth mentioning that when the electrode skin treating tip 304 is used, the fluid delivery will not be turned off. Therefore, no aperture 224 and vacuum entry port 226 is formed at the electrode skin treating tip 304.

An embodiment in FIG. 14 illustrates a further modification of the tip 404 that detachably couples to the handle 102. The tip 404 is a micro-needle skin treating tip, which is also the multi-functional tip 204 to provide multiple functions. Similar to the multi-functional tip 204 in FIG. 7, the micro-needle skin treating tip 404 has a slanted skin applying surface, wherein the outer structure 242, intermediate structure 444, and the inner structure 246 are coaxial with each other and are formed at the slanted skin applying surface. The outer structure 242 of the tip 404 comprises the abrading structure 232. The inner structure 246 comprises the fluid delivery tip 222 and vacuum entry port 226. The difference between the multi-functional tip 204 and the micro-needle skin treating tip 404 is that the intermediate structure 444 comprises a micro-needle assembly 430 having a plurality of micro-needles 431 provided at the skin applying surface between the outer structure 242 and the inner structure 246.

The micro-needle assembly 430 is another embodiment structure to penetrate fluid delivered through the skin that further comprises a vibrator 432 supported in the tip 404. The vibrator 432 is connected to the control circuit 138 and is linked to the micro-needles 431. During operation, the vibrator 432 will generate a vibration force to vibrate the micro-needles 431, so that the micro-needles 431 will drive to reciprocatingly move and puncture into the skin surface. The vibrator 432 can also be a sonic vibrator to generate sonic wave to vibrate the micro-needles 431. Therefore, the micro-needle skin treating tip 404 provides a micro-needling treatment for improving the skin complexion, wrinkle reduction and facial rejuvenation. The micro-needle skin treating tip 404 will repair skin damage from the sun, from acne, from injuries etc. By making tiny puncture wounds in the skin via the micro-needles 431, causes a wound healing reaction that stimulates the skin to produce collagen to repair the controlled injury. The micro-needle assembly 430 further comprises a needle leveling adjustor 433 provided at the sidewall of the tip 404, wherein the level of depth of the micro-needles 431 can puncture the skin will be adjusted by the needle leveling adjustor 433.

FIG. 15 shows another alternative embodiment of the micro-needle skin treating tip 504. The micro-needle skin treating tip 504 has a slanted skin applying surface, wherein the outer structure 242, intermediate structure 544, and the inner structure 546 are coaxial with each other and are formed at the slanted skin applying surface. The outer structure 242 of the tip 504 comprises the abrading structure 232.

The intermediate structure 544 comprises the fluid delivery structure having an aperture 524, a vacuum entry port 526, and an additional vacuum entry port 526a.

The inner structure 546 further comprises a fluid delivery wall 545 extended between the aperture 524 and the vacuum entry port 526 to form a fluid detouring path. When the fluid is ejected from the aperture 524, the fluid is guided and detoured along the fluid detouring path to the vacuum entry port 526. Therefore, the fluid detouring path will prolong the traveling distance of the fluid from the aperture 524 to the vacuum entry port 526. The fluid delivery wall 545 is extended between two opposite sides of the boundary wall that partitions the intermediate structure 544 into a loop structure, wherein the aperture 524 and the vacuum entry port 526 are located at two ends of the fluid detouring path respectively, so that the fluid travels around the inner structure 546 from the aperture 524 to the vacuum entry port 526.

The inner structure 546 comprises a micro-needle assembly 530 having a plurality of micro-needles 531 provided at the skin applying surface within the inner structure 546. The vibrator 432 and the needle leveling adjustor 433 as disclosed in FIG. 14 will also be employed in the micro-needle assembly 530. So, the vibrator 432 will generate a vibration force to vibrate the micro-needles 531, so that the micro-needles 531 will drive reciprocatingly to puncture into the skin surface. The level of the micro-needles 531 will be adjusted by the needle leveling adjustor 433 in order to adjust how deep the micro-needles 431 will to be punctured into the skin surface.

The multi-functional tip 204, the electrode skin treating tip 304, and the micro-needle skin treating tips 404, 504 are interchangeable.

FIG. 16 shows another embodiment of the apparatus of the invention. The apparatus for transdermal fluid delivery comprises a handle 610, a multi-functional tip 620, a fluid delivery structure 630, and a tip driver 640.

The handle 610 in this embodiment is an angled handle which comprises a casing 612 and a hand grip 614 inclined and extended from the casing 612. The casing 612, which is a hollow casing, has a front working end and a rear communicating end. The hand grip 614 is extended from the casing 612 between the working end and the communicating end, wherein an angle between the casing 612 and the hand grip 614 should be less than 90 degrees. The casing 612 comprises a detachable cap 616 detachably coupled at the casing 612, wherein the working end is defined at the detachable cap 616. The working end of the detachable cap 616 has a crown shaped outer edge 618 to apply pressure on the skin to perform pressure extractions.

The handle 610 is ergonomically designed, wherein the handle 610 can be held by a right or left-handed user. The casing 612 can be held by the thumb and the index finger of the user and the hand grip 614 can be held by the middle finger, ring finger, little finger and palm as illustrated in FIG. 16. During operation of the device, the palm of the user may not be resting on a surface being treated. The angled handle 610 will give the fingers of the user more precise control of the working end of the casing 612 by the support of the palm of the user. That is to say, the palm support at the hand grip 614 will relieve the pressure at the fingers when held at the casing 612.

The multi-functional tip 620 has a skin applying surface located at the working end of the handle 610, wherein the skin applying surface is capable of contacting with a user skin. In FIG. 16, a plurality of abrading elements 622 are provided at the skin applying surface. In alternative mode, a micro-needle assembly 624 having a plurality of micro-needles is provided at the skin applying surface.

The multi-functional tip 620 further comprises an electrode module comprising a plurality of electrodes 626 encircled around the skin applying surface in a detachably mounting manner. The electrodes 626 are arranged in a ring configuration to surround the skin applying surface. The electrodes 626 are built-in with an inner side of the detachable cap 616 adjacent to the crown shaped outer edge 618 thereof. Therefore, the electrodes 626 can be replaced, detached, and/or disposed by the detachable engagement of the detachable cap 616. That is to say, the electrodes 626 of the electrode module will be located around the abrading elements 622 and/or the micro-needle assembly 624 on the skin applying surface. A vacuum inlet 621 is formed between the electrodes 626 of the electrode module and the abrading elements 622/the micro-needle assembly 624.

The electrodes 626 will generate a desired function, such as iontophoresis, electroporation, ultrasound, or photomechanical wave. For electroporation, high voltage current is applied to the skin producing hydrophilic pores in the intercellular bilayers via momentary realignment of lipids. For phonophoresis, ultrasound pulses are passed through the probe into the skin fluidizing the lipid bilayers by the formation of bubbles caused by cavitation. For iontophoresis, a current passed between the active electrode and the indifferent electrode repelling drug away from the active electrode and into the skin. All the electrodes 626 can be configured to provide the same desired function. Or, each of the electrodes 626 can be configured to provide a particular function, so that the electrodes 626 will provide different functions at the same time when contacting with the skin. Therefore, different electrical frequencies are generated to stimulate different and wider range of cells types and skin depths from the surface to underneath so as to cause multiple reactions from the skin.

FIGS. 16 and 17 show the tip driver 640 secured and supported in the casing 612 between the working end and the communicating end. The tip driver 640 comprises a driving unit 642 supported in the casing 612 and a driving shaft 644 operatively extended from the driving unit 642 to the multi-functional tip 620. The driving unit 642 is operated to generate a movement at the skin applying surface of the multi-functional tip 620 via the driving shaft 644. For example, with the abrading elements 622 on the skin applying surface, the driving unit 642 will drive the skin applying surface of the multi-functional tip 620 to rotate via the driving shaft 644. It is preferred the driving unit 642 will generate a reciprocating movement to rotate the multi-functional tip 620 back and forth. With the micro-needle assembly 624 on the skin applying surface, the driving unit 642 will drive the skin applying surface of the multi-functional tip 620 to slide within the casing 612 via the driving shaft 644. It is preferred the driving unit 642 will generate a reciprocating movement to move the multi-functional tip 620 front and back, which is aligned with a centerline of the casing 612. During the operation of the device, the user will hold the handle 610 stably and stationary, and the skin applying surface of the multi-functional tip 620 is driven to move to contact with the user's skin.

The driving shaft 644 has at least a hollow portion extended to the multi-functional tip 620. It is preferred the driving shaft 644 is made of stainless steel.

FIGS. 16 and 17 further show the fluid delivery structure 630 to guide a flow of fluid to the skin applying surface of the multi-functional tip 620. The fluid delivery structure 630 has a fluid channel 632 defined at the hollow portion of the driving shaft 644 and at least an aperture 634 formed on the skin applying surface of the multi-functional tip to communicate with the fluid channel 632. Therefore, the driving shaft 644 has a multifunction of driving the skin applying surface of the multi-functional tip to move and also while guiding the fluid through the fluid channel 632 to the skin applying surface of the multi-functional tip 620 at the aperture 634 at the same time.

The fluid will be directly ejected right on the skin applying surface of the multi-functional tip 620 at the aperture 634 when the skin applying surface of the multi-functional tip 620 is contacted with the user skin, so that the fluid delivery structure 630 of the invention is the most optimal way to transdermally penetrate fluid deeper in the skin.

In FIG. 16, the aperture 634 is located at the center of the skin applying surface of the multi-functional tip 620, wherein the abrading elements 622 are radially formed at the skin applying surface. A plurality of fluid distributing channels 628 are radially and outwardly extended from the aperture 634 to the electrodes 626. Each of the fluid distributing channels 628 is formed at a gap between two adjacent abrading elements 622. Therefore, the fluid will be evenly distributed on the skin applying surface through the fluid distributing channels 628 and toward the electrodes 626. It is realized that the apertures 634 can also be located in other areas other than the center of the skin applying surface within the abrading elements 622, such as the sides as well.

In FIG. 16, two or more of apertures 634 can be provided at the skin applying surface to deliver the fluid to the micro-needle assembly 624. Two or more of apertures 634 can also be provided at the skin applying surface and can serve as a jet propulsion outlet to deliver the fluid in a high rate of speed.

In FIG. 16, the multi-functional tip 620 is detachably coupled at the free end of the driving shaft 644. When the multi-functional tip 620 is detachably coupled at the free end of the driving shaft 644, the aperture 634 is communicatively linked to the fluid channel 632. Therefore, different types of multi-functional tip 620 are interchangeable and coupled at the driving shaft 644. In this embodiment, three different types of multi-functional tip 620 are provided, i.e. the multi-functional tip 620 with the abrading elements 622, the multi-functional tip 620 with the micro-needle assembly 624, and the multi-functional tip 620 with the jet propulsion outlet. All these multi-functional tips 620 can be detachably coupled at the driving shaft 644 to guide the fluid to be ejected at the skin applying surface.

In FIGS. 17 and 18, the fluid delivery structure 630 further has at least a fluid inlet 636 transversely formed at the driving shaft 644 to guide the fluid entering into the fluid channel 632 from the fluid inlet 636 and to guide the fluid exiting toward the aperture 634. It is preferred two fluid inlets 636 are formed at the driving shaft 644 are perpendicular to the fluid channel 632.

In FIGS. 16 and 17, the device further comprises a support member 650 secured and supported in the casing 612 in a non-movable manner. The support member 650 can be removably mounted in the casing 612 to support the driving unit 642. The support member 650 has a through center slot 652, wherein the driving shaft 644 is supported by and extended through the center slot 652 of the support member 650. In this embodiment, the driving shaft 644 is movable and the support member 650 is stationary. During the operation of the driving unit 642, the driving shaft 644 will be moved and vibrated at any direction. The support member 650 will restrict the movement of the driving shaft 644 in only one direction. For example, the support member 650 will ensure the driving shaft 644 to be rotated within the center slot 652 or to be slid back and forth within the center slot 652. So, the support member 650 will prevent any unwanted vibration of the driving shaft 644. The support member 650 also supports the driving shaft 644 in the casing 612 because the driving shaft 644 must be long enough to extend from the driving unit 642 to the mufti-functional tip 620 within the casing 612. Therefore, the support member 650 is located between the driving unit 642 and the multi-functional tip 620, wherein the rear side of the support member 650 faces toward the driving unit 642 and the front side of the support member 650 faces toward the multi-functional tip 620.

In FIGS. 17 and 18, the fluid inlet 636 at the driving shaft 644 is located within the support member 650. To guide the fluid into the fluid inlet 636 through the support member 650, the support member 650 has an interior fluid cavity 654 for delivering the fluid from a fluid source to the interior fluid cavity 654. Then, the fluid in the interior fluid cavity 654 will enter into the fluid channel 632 from the fluid inlet 636. The interior fluid cavity 654 is radially projected from the center slot 652 of the support member 650, so that when the driving shaft 644 is extended through the center slot 653, the fluid inlet 636 can communicate with the interior fluid cavity 654.

As the driving shaft 644 is movable and extended through the center slot 652 of the support member 650 to locate the fluid inlet 636 within the interior fluid cavity 654 of the support member 650, the fluid is able to enter into the fluid inlet 636 from the interior fluid cavity 654 when the driving shaft 644 is moved with respect to the support member 650.

The size of the interior fluid cavity 654 is configured in response to the movement of the driving shaft 644. When the driving shaft 644 is rotated within the center slot 652, the width of the interior fluid cavity 654 should be larger than a diameter of the fluid inlet 636. When the driving shaft 644 is slid within the center slot 652, the width of the interior fluid cavity 654 should be larger than a traveling displacement of the fluid inlet 636.

Two sealing elements 656 are embedded at an inner wall of the center slot 652 to fluidly seal the fluid inlet 636 within the interior fluid cavity 654 and between the two sealing elements 656. The sealing elements 656 are two sealing rings embedded in the inner wall of the center slot 652 to engage with the driving shaft 644, wherein the driving shaft 644 is still movable when the sealing elements 656 are engaged with the driving shaft 644. The sealing element 656 will only seal the fluid within the interior fluid cavity 654 to prevent the leakage of the fluid within the center sot 652 when the driving shaft 644 is moved.

In FIGS. 16, 17, and 18, the support member 650 further has a fluid guiding passage 658 extended from the rear side of the support member 650 to the interior fluid cavity 654, wherein the fluid is guided to flow from the fluid guiding passage 658 to the interior fluid cavity 654 before it is guided to flow to the fluid channel 632 from the fluid inlet 636. The fluid guiding passage 658 is an elongated passage. An inlet of the fluid guiding passage 658 is formed at the rear side of the support member 650 and an outlet of the fluid guiding passage 658 is formed at the interior fluid cavity 654. A first fluid tube 662 is extended from the inlet of the fluid guiding passage 656 and is extended out of the communicating end of the casing 612 to operatively link to the fluid source.

The fluid delivering path of the fluid from the fluid source to the skin applying surface of the multi-functional tip 620 is described as follows. The fluid is stored in the fluid source and is guided to flow from the fluid source to the fluid guiding passage 658 by the first fluid tube 662. The fluid source may generate an optional pumping force to pump the fluid to the fluid guiding passage 658. The fluid is then guided into the interior fluid cavity 654 by the fluid guiding passage 658. The fluid will enter into the fluid channel 632 from the fluid inlet 636. Finally, the fluid will be delivered right on the skin applying surface of the multi-functional tip 620 at the aperture 634. Without the pumping force generated by the fluid source, the fluid is pulled from the fluid source, through the fluid guiding passage 658, the interior fluid cavity 654, to delivered right on the skin applying surface of the multi-functional tip 620 at the aperture 634 by the vacuum source.

The support member 650 further has a vacuum passage 657 extended through the support member 650 and a vacuum port 659 for vacuuming the fluid after the fluid is delivered to the skin applying surface of the multi-functional tip 620. An inlet of the vacuum passage 657 is formed at the front side of the support member 650 and an outlet of the vacuum passage 657 is formed at the rear side of the support member 650. It is preferred that the vacuum port 659 is extended from the inlet of the vacuum passage 657 toward the vacuum inlet 621 around the skin applying surface of the multi-functional tip 620. A second fluid tube 666 is extended from the outlet of the vacuum passage 657 and is extended out of the communicating end of the casing 612 to operatively link to a fluid reservoir.

The fluid returning path of the fluid from the skin applying surface of the multi-functional tip 620 to the fluid reservoir is described as follows. The used fluid at the working end of the casing 612 is collected at the vacuum inlet 621 by the vacuum port 659 and is transmitted to the vacuum passage 657. Then, the used fluid will be delivered to a fluid reservoir by the second fluid tube 666. The fluid reservoir will generate a vacuum force to create a vacuum effect at the vacuum port 659. When the fluid is delivered at the skin applying surface of the multi-functional tip 620, the fluid will be electrified and conducted with the electrodes 626.

In FIG. 17, the center slot 652, the fluid guiding passage 658, and the vacuum passage 657 are parallel with each other at the support member 650. It is important that the fluid will pass the electrodes 626 from the skin applying surface before the fluid is pulled back at the vacuum inlet 621, so that the fluid will be electrified and conducted with the electrodes 626 to enable the liquid to penetrate into the skin longer and deeper.

A control module 670 is provided to control the operations of the electrodes 626 and the tip driver 640. The control module 670 comprises a control circuit 672 operatively connected to the electrodes 626 and the tip driver 640, and a transmission unit 674, such as a gear box, operatively connected to the driving unit 642 to adjust amplitude of the driving shaft 644. For example, the output of the rotational speed (rpm) of the driving unit 642 can be adjusted by the transmission unit 674, so that the user is able to adjust the rotational speed of the multi-functional tip 620 via one or more control switches 676 provided on the handle 620. The control switches 676 can also control and select the electrical frequencies of the electrodes 626. An insulated wiring 627 is provided to connect the electrodes 626 with the control module 670 and is embedded in the detachable cap 616 to prevent the electric shock when the fluid is pulled back from the vacuum inlet 621. A terminal is provided at the rear end of the detachable cap 616 to connect with the insulated wiring 627, so that when the detachably cap 616 is detachably coupled at the casing 612, the electrodes 626 are electrically connected to the control module 670. It would be acceptable that the electrodes 626 are replaceable, detachable, and/or disposable by interchanging different detachable caps 616. The control module 670 can also be located on the main unit (not shown) controlled by manual push button switches or controlled by a touch screen monitor that is connected to the handle 610.

An alternative of the device can be formed without the driving unit, wherein the multi-functional tip 620 is driven to move by the flow of the fluid via the fluid delivery structure 630. For example, when the fluid is guided to flow at the fluid channel 632 in a vortex manner to drive the multi-functional tip 620 to rotate. Or the apertures 634 on the skin applying surface have an ejecting angle, so that during the ejection of fluid at the apertures 634, the multi-functional tip 620 is propelled to rotate.

FIG. 19 shows a modification of the electrode module which comprises two or more different electrodes 726. In FIG. 19, three different electrodes 726 are utilized and are configured into an inner electrode ring, an intermediate electrode ring, and an outer electrode ring which are coaxial with the skin applying surface of the multi-functional tip 620 orderly. The three electrode rings will generate different electrical frequencies to stimulate different and wider range of cells types and skin depths from the surface to underneath so as to cause multiple reactions from the skin. That is to say, the three different electrodes 726 can improve the skin structure affecting multiple layers of the skin, such as, epidermis, dermis, and hypodermis. It is worth mentioning that the fluid will guide to pass through different electrodes 726 from the abrading elements 622 on the skin applying surface to the vacuum inlet 621 at the perimeter of the outer electrode ring.

The apparatus of the present invention is an innovative apparatus of treating the skin to transdermally penetrate fluid deeper into the skin by means of simultaneous (1) abrasive peeling via the abrading elements 622, (2) electrical stimulation via the electrodes 626, (3) liquid infusion via the fluid delivered onto the skin applying surface, in order to improve the skin structure affecting multiple layers of the skin, such as, epidermis, dermis, and hypodermis.

More importantly, the fluid will be delivered right on the skin applying surface to evenly distribute on the abrading elements 622 and then to electrify with the electrodes 626 before the fluid is vacuumed back through at the vacuum inlet 621. The traveling path of the fluid will be prolonged between the aperture 634 and the vacuum inlet 621 to ensure the fluid to pass through the abrading element 622 and the electrodes 626. The skin abrading operation is automatic by the movement of the multi-functional tip 620. Therefore, the apparatus of the present invention produces a new singular treatment to include three different skin treatment methods in one single device. That is to say, the user can simply hold the handle 610 stationary and place the skin applying surface of the multi-functional tip 620 on the skin surface with three different functions operating in conjunction with each other.

Therapeutically, when the interaction between the fluid and electrodes 626 occurs, it delivers a medicine in the fluid through the skin surface. It is a non-invasive method to enhance the effects on skin permeation and to enhance the absorption of medicine across the skin surface. It drives a charged substance, such as medication or a bioactive agent, transdermally by repulsive electromotive force, through the skin surface.

The three different skin treatment methods are interlinked with each other and are not independent functions from each other. That is to say, the three different skin treatment methods enhance each other's functions as a whole. The fluid will be delivered right on the skin applying surface to directly contact with the skin surface for liquid infusion. The fluid will also be flush to the skin surface when the abrading elements 622 are applied on the skin surface. The fluid will also interact with the electrodes 626 for electrical stimulation on the skin surface. It is worth mentioning that due to the vacuum effect at the vacuum inlet 621, the fluid will be forced to vacuum at the vacuum inlet 621 from the apertures 634 to ensure the fluid to pass through the abrading elements 622 and the electrodes 626 before the fluid is pulled back at the vacuum inlet 621.

The method of the present invention for transdermal fluid delivery comprises the steps as follows:

(A) Hold the handle 610 stationary to locate the working end of the handle 610 on a skin surface.

(B) Deliver the fluid onto the skin applying surface of the multi-functional tip 620 at the aperture 634 which is formed on the skin applying surface. Therefore, the fluid can be directly delivered to the skin applying surface to contact with the skin surface. More particularly, the fluid is guided to pass through the hollow portion of the driving shaft 644 which serves as the fluid channel 632 to guide the fluid to the aperture 634 through the fluid channel 632.

(C) Evenly distribute the fluid on the abrading elements 622 which are provided on the skin applying surface. The fluid can be evenly distributed on the abrading elements 622 through the fluid distributing channels 628. Or, two or more apertures 634 are formed on the skin applying surface to evenly distribute on the abrading elements 622.

(D) Drive the skin applying surface of the multi-functional tip 620 to move for abrasive peeling while the handle 610 is stationary. Without moving the handle 610, the skin applying surface of the multi-functional tip 620 is driven to move by the tip driver 640.

(E) Guide the fluid to be interacted with the electrodes 626 of the electrode module encircled around the skin applying surface. After the fluid interacting with the abrading elements 622, the fluid will pass to the electrodes 626 for electrical stimulation on the skin surface.

(F) Vacuum back the fluid at the vacuum inlet 621 formed at the perimeter of the electrode module to ensure the fluid to interact the abrading elements 622 and the electrodes 626 before the fluid is pulled back at the vacuum inlet 621. Due to the vacuum effect, the fluid will be forced to pass through the abrading elements 622 and the electrodes 626.

Although the present invention has been discussed in considerable detail with reference to certain preferred embodiments, other embodiments are possible. Therefore, the scope of the appended claims should not be limited to the description of preferred embodiments contained herein.

While the embodiments and alternatives of the invention have been shown and described, it will be apparent to one skilled in the art that various other changes and modifications can be made without departing from the spirit and scope of the invention.

What is claimed is:

1. An apparatus for transdermal fluid delivery, comprising;
    a multi-functional tip having a skin-applying surface, a support member within a handle structure, comprising, a fluid delivery structure, a fluid returning structure and a tip driver;
    wherein said skin applying surface of said multifunctional tip comprises a plurality of abrading elements and a plurality of electrodes encircling said abrading elements;
    wherein said support member comprising said fluid delivery structure, said fluid returning structure and said tip driver is secured inside a casing within said handle structure;
    wherein said tip driver comprises, a driving unit and a driving shaft;
    wherein said driving shaft is operatively extended from said driving unit to said multi-functional tip through a center slot of said support member, wherein said driving shaft is movable and said support member is stationary;
    wherein said multifunctional tip comprising said plurality of abrading elements and said plurality of electrodes is detachably coupled at a free end of said driving shaft;
    wherein said driving shaft has at least a hollow portion extended to said multi-functional tip, wherein a fluid delivery channel of said fluid delivery structure is defined at said hollow portion of said driving shaft;
    wherein said fluid delivery structure further has a fluid inlet transversely formed at said driving shaft to guide a fluid from an interior fluid cavity of said support member into said fluid delivery channel defined at said hollow portion of said driving shaft,
    wherein said fluid delivery structure has at least an aperture located at an axial center of said skin applying surface of said multi-functional tip to communicate with said fluid delivery channel defined at said hollow portion of said driving shaft and deliver fluid to the skin surface;
    wherein said driving shaft has a dual function of driving said skin applying surface of said multi-functional tip to rotate while concomitantly guiding a flow of a fluid through said fluid delivery channel to said skin applying surface of said multi-functional tip at said aperture;
    wherein said driving unit is operated to generate a movement by a motor at said skin applying surface of said multi-functional tip through said driving shaft; and
    wherein said fluid returning structure comprises a vacuum inlet, a vacuum port and a vacuum passage, wherein said vacuum passage is extended through said support member to transport a used fluid collected by said vacuum inlet from said multifunctional tip by said vacuum port to a reservoir at a rear end of said support member.

2. The apparatus in claim 1 wherein said support member is stationary and restricts a movement of said driving shaft within said center slot of said support member only in one direction or back and forth within said center slot said support member there preventing any unwanted vibrations of said driving, shaft when it is in operation.

3. The apparatus in claim 1 wherein said driving shaft is movable and extended through said center slot of said support member to locate said fluid inlet within said interior fluid cavity of said support member, so that when said driving shaft is moved with respect to said support member, said fluid is able to enter into said fluid inlet from said interior fluid cavity of said support member.

4. The apparatus in claim 1 wherein said support member further comprises two sealing elements embedded at an inner wail of said center slot of said support member to fluidly seal said fluid inlet within said interior fluid cavity between said two sealing elements to prevent leakage of said fluid within said center slot of said support member when the driving shaft moves.

5. The apparatus in claim 1 wherein said support member further has a fluid guiding passage extended from a rear side of said support member to said interior fluid cavity, wherein said fluid is guided to flow from said fluid guiding passage to said interior fluid cavity before it is guided to flow into said fluid delivery channel from said fluid inlet.

6. The apparatus in claim 1 wherein said aperture formed at said axial center of said skin applying surface defines a plurality of fluid distributing channels radially and outwardly extended from said aperture to said electrodes, wherein each of said fluid distributing channels is formed at it gap between two adjacent abrading elements.

7. The apparatus in claim 1 wherein said multi-functional tip further comprises a micro-needle assembly having a plurality of micro-needles provided at said skin applying surface.

8. An apparatus for transdermal fluid delivery, comprising:
- a handle, having a working end with a multi-functional tip having a skin applying surface, comprising a plurality of abrading elements and an electrode module comprising a plurality of electrodes encircled around said plurality of abrading elements;
- a support member comprising, a tip driver, a fluid delivery structure and a fluid returning structure;
- wherein said tip driver comprises a driving unit and a driving shaft operatively extended from said driving unit to said multi-functional tip through a center slot of said support member, for generating a movement at said skin applying surface of said multi-functional tip;
- wherein said driving shaft is movable and said support member is stationary;
- wherein said multifunctional tip comprising said plurality of abrading elements and said electrode module comprising it plurality of electrodes encircled around said plurality of abrading elements is detachably coupled at a free end of said driving shaft at said working end of said handle;
- wherein a fluid delivery channel is defined at a hollow portion of said driving shaft that is extended to said multifunctional tip and at least an aperture located at ail axial center within said plurality of abrading elements at said multifunctional tip, to deliver fluid to a skin surface;
- wherein a fluid within an interior fluid cavity of said support member enters a fluid inlet transversely formed at said driving shaft when the driving shaft rotates with respect to said support member by means of said driving unit; a plurality of fluid distributing channels radially and outwardly extended from said aperture located within said axial center of said plurality of abrading elements to said electrodes so that a fluid is evenly distributed on a skin surface and said electrodes; and
- wherein said fluid returning structure has a vacuum inlet formed at a perimeter of said electrode module, wherein a fluid traveling path is defined between said aperture located at said axial center and said vacuum inlet for ensuring a flow of fluid to be delivered onto said skin applying surface through said aperture and to interact with said abrading elements and said electrodes before said fluid is pulled back through said vacuum inlet through a vacuum port, so that three different functions of skin treatments of abrasive peeling, electrical stimulation, and liquid infusion are achieved in one step.

9. A method for transdermal fluid delivery, comprising the steps of:
- (a) holding a handle stationary to place a working end of said handle on a skin surface;
- (b) delivering a flow of fluid onto said skin surface through an aperture on a multi-functional tip having a plurality of rotating and vibratory abrading elements located at said working end of said handle;
- (c) evenly distributing said fluid through said plurality of rotating and abrading elements on said multi-functional tip onto said skin applying surface;
- (d) a driving shaft driving said multi-functional tip to rotate and or vibrate said plurality of rotating and vibratory abrading elements to abrade said skin applying surface while said handle remains stationary;
- (e) simultaneously, guiding said fluid to interact with a plurality of electrodes on an electrode module encircled around an inner structure of the multi-functional tip.

10. The method in claim 9 further comprising a step (f) of pulling back said fluid at a vacuum inlet formed at a perimeter of said electrode module to ensure said fluid to interact with said abrading elements and said electrodes before said fluid is pulled back at said vacuum inlet and removing a used fluid from said multifunctional tip to a reservoir at a rear end of said handle.

\* \* \* \* \*